US007279466B2

(12) United States Patent
Pettit et al.

(10) Patent No.: US 7,279,466 B2
(45) Date of Patent: Oct. 9, 2007

(54) SYNTHESIS OF COMBRETASTATIN A-4 PRODRUGS AND TRANS-ISOMERS THEREOF

(75) Inventors: George R. Pettit, Paradise Valley, AZ (US); Monte R. Rhodes, Humble, TX (US)

(73) Assignee: Arizona Board of Regents, Tempe, AZ (US)

( * ) Notice: Subject to any disclaimer, the term of this patent is extended or adjusted under 35 U.S.C. 154(b) by 0 days.

(21) Appl. No.: 11/364,733

(22) Filed: Feb. 27, 2006

(65) Prior Publication Data

US 2007/0073077 A1    Mar. 29, 2007

Related U.S. Application Data

(63) Continuation of application No. 09/582,950, filed as application No. PCT/US99/00419 on Jan. 8, 1999, now Pat. No. 7,018,987.

(60) Provisional application No. 60/071,070, filed on Jan. 9, 1998, provisional application No. 60/111,531, filed on Dec. 9, 1998.

(51) Int. Cl.
*A61K 31/66* (2006.01)
*C07F 9/02* (2006.01)
(52) U.S. Cl. ...................... 514/130; 558/197
(58) Field of Classification Search .............. None
See application file for complete search history.

(56) References Cited

U.S. PATENT DOCUMENTS 5,484,799 A    1/1996   Hochlowski et al. ....... 514/345

OTHER PUBLICATIONS

Petit et al, Anti-Cancer Drug Design, Antineoplastic agents. 322. Synthesis of combretastatin A-4 prodrugs, 1995, 10(4), pp. 299-309.*
CA:123:227731 abs of Anti Cancer Drug Design by Pettit et al. 10(4) pp. 200-309 (1995).
Atherton et al., "Studies on Phosphorylation. Part III. Further Observations on the Reaction of Phosphites with Polyhalogen Compounds in Presence of Bases and its Application to the Phosphorylation of Alcohols", *Journal of the Chemical Society*, pp. 674-678, (1947).
Brown, R.T.; Fox, B.W.; Hadfield, J.A.; McGown, A.T.; Mayalarp, S.P.; Pettit, G.R.; and Woods, J.A., "Synthesis of Water-Soluble Sugar Derivatives of Combretastatin A-4", *Journal of the Chemical Society, Perkin Transactions I*, vol. _(1995), pp. 577-.
Bedford, S.B.; Quarterman, C.P.; Rathbone, D.L.; Slack, J.A.; Griffin, R.J.; and Stevens, M.F.G., "Synthesis of Water-Soluble Prodrugs of the Cytotoxic Agent Combretastatin A-4" *Bioorganic & Medicinal Chemistry Letters*, vol. 6, No. 2, pp. 157-160, (1996).
Silverberg, L.J.; Dillon, J.L.; Vemishetti, P., "A Simple, Rapid and Efficient Protocol for the Selective Phosphorylation of Phenols with Dibenzyl Phosphite", *Tetrahedron Letters*, vol. 37, No. 6, pp. 771-774 (1996).
Dorr, R.T.; Dvorakova, K.; Snead, K.; Alberts, D.S.; Salmon, S.E.; Pettit, G.R., "Antitumor activity of combretastatin A-4 Phosphate, A Natural Product Tubulin Inhibitor", *Investigational New Drugs*, vol. 14, pp. 131-137 (1996).
Pettit, G.R.; Rhodes, M.R., "Antineoplastic Agents 389. New Syntheses of the Combretastatin A-4 Prodrug", *Anti-Cancer Drug Design*, vol. 13, No. 3, pp. 183-191 (1998).
Pettit, G.R.; Rhodes, M.R., "Antineoplastic Agents 393. Synthesis of the *trans*-isomer of Combretastatin A-4 Prodrug", *Anti-Cancer Drug Design*, vol. 13, No. 8, pp. 981-993 (1998).
Pettit, G.R.; Toki, B.; Herald, D.L.; Verdier-Pinard, P.; Boyd, M.R.; Hamel, E.; and Pettit, R.K., "Antineoplastic Agents. 379. Synthesis of Phenstatin Phosphate", *Journal of Medicinal Chemistry*, vol. 41, No. 10, pp. 1688-1695 (1998).
Ohsumi, K.; Hatanaka T.; Nakagawa, R.; Fukuda, Y.; Morinaga, Y.; Suga, Y.; ;Nihei, Y.; Ohishi, K.; Akiyama, Y.; and Tsuji, T., "Synthesis and Antitumor Activities of Amino Acid Prodrugs of Amino-Combretastatins", *Anti-Cancer Drug Design*, vol. 14, pp. 539-548 (1999).
Pettit, G.R.; Lippert III, J.W., "Antineoplastic Agents 429. Syntheses of the Combretastatin A-1 and Combretastatin B-1 Prodrugs", *Anti-Cancer Drug Design*, vol. 15, No. 3, pp. 203-216 (2000).
Pettit, G.R.; Lippert III, J.W.; Boyd, M.R.; Verdier-Pinard, P.; and Hamel, E., "Antineoplastic Agents 442. Synthesis and Biological Activities of Dioxostatin", *Anti-Cancer Drug Design*, vol. 15, No. 4, pp. 361-371 (2000).
Pettit, G.R.; Minardi, M.D.; Boyd, M.R.; and Pettit, R.K., "Antineoplastic Agents 463. Synthesis of Combretastatin A-3 Diphosphate Prodrugs", *Anti-Cancer Drug Design*, vol. 15, No. 4, pp. 397-403 (2000).
Pettit, G.R.; Graelish, M.P.; Jung, M. K.; Hamel, E.; Pettit, R.K.; Chapuis, J.-C.; and Schmidt, J.M., "Antineoplastic Agents. 465. Structural Modification of Resveratrol: Sodium Resverastatin Phosphate", *Journal of Medicinal Chemistry*, vol. 45, No. 12, pp. 2534-2542 (2002).
Hill, S.A.; Chaplin, D.J.; Lewis, G.; Tozer, G.M., "Schedule Dependence of Combretastatin A-4 Phosphate in Transplanted and Spontaneous Tumour Models", *International Journal of Cancer*, vol. 102, No. 1, pp. 70-74 (2002).
Dowlati, A.; Robertson, K.; Cooney, M.; Petros, W.P.; Stratford, M.; Jesberger, J., et al., "A Phase I Pharmacokinetic and Translational Study of the Novel Vascular Targeting Agent Combretastatin A-4 Phosphate on a Single-Dose Intravenous Schedule in Patients with Advanced Cancer", *Cancer Research*, vol. 62, pp. 3408-3416 (Jun. 15, 2002).
Nabha, S.M.; Mohammad, R.M.; Dandashi, M.H.; Coupaye-Gerard, B.; Aboukameel, A.; Pettit, G.R.; and Al-Katib, A.M., "Combretastatin A-4 Prodrug Induces Mitotic Catastrophe in Chronic Lymphocytic Leukemia Cell Line Independent of Caspase Activation and Poly(ADP-ribose) Polymerase Cleavage", *Clinical Cancer Research*, vol. 8, pp. 2735-2741 (Aug. 2002).

(Continued)

*Primary Examiner*—Paul A. Zucker
(74) *Attorney, Agent, or Firm*—Fennemore Craig, P.C.

(57) ABSTRACT

Combretastatin A-4 has been previously selected for preclinical development as antineoplastic agent. However, it is essentially insoluble in water. New water soluble derivatives of combretastatin A-4 and its qualified analogs have been discovered and synthesized through a multistage process using other derivatives of combretastatin A-4 as intermediates. These water soluble derivatives are herein denominated as "Combretastatin A-4 Prodrugs".

18 Claims, 2 Drawing Sheets

OTHER PUBLICATIONS

Hadiman, M.B., et al., "Synthesis, In Vitro, and In Vivo Evaluation of Phosphate Ester Derivatives of Combretastatin A-4", *Bioorganic & Medicinal Chemistry Letters*, vol. 13, No. 9, pp. 1505-1508 (2003).

Ahmed, B.; Van Euk, L.I., et al., "Vascular Targeting Effect of Combretastatin A-4 Phosphate Dominates the Inherent Angiogenesis Inhibitory Activity", *International Journal of Cancer*, vol. 105, No. 1, pp. 20-25 (2003).

* cited by examiner

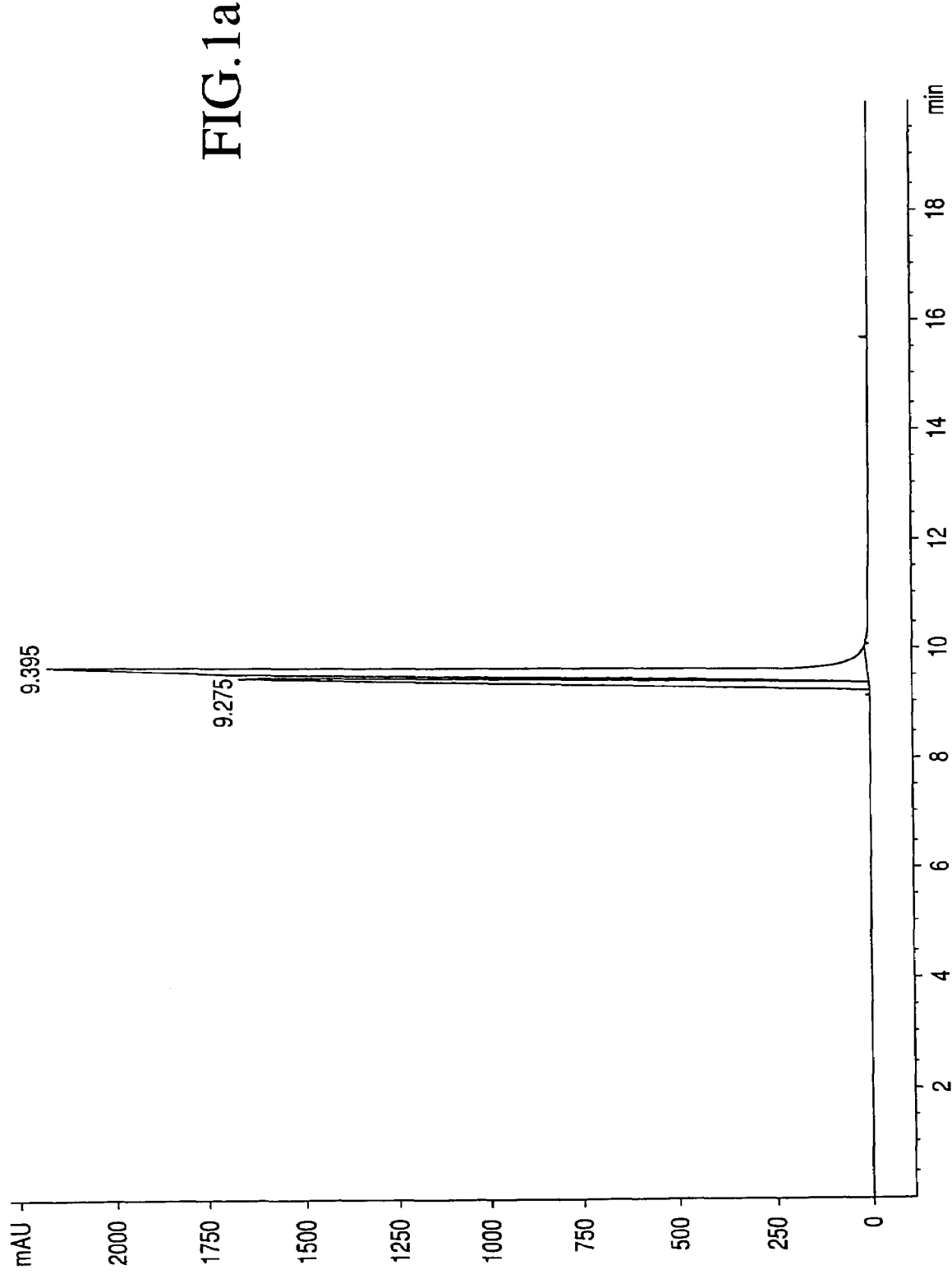

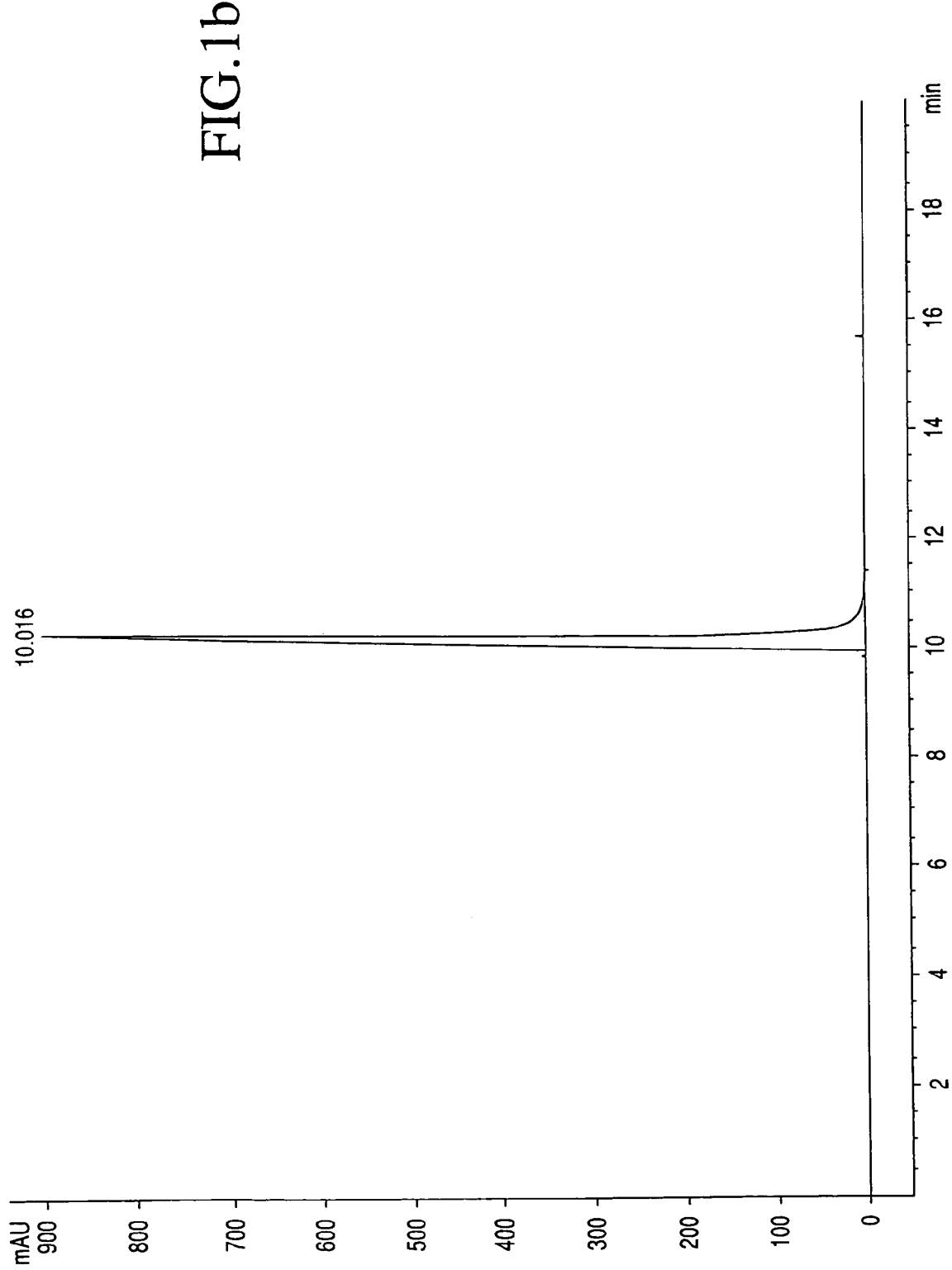

SYNTHESIS OF COMBRETASTATIN A-4 PRODRUGS AND TRANS-ISOMERS THEREOF

RELATED APPLICATION DATA

This application is continuation of U.S. Nonprovisional Application Ser. No. 09/582,950, now U.S. Pat. No. 7,018,987, filed on Jul. 7, 2000, which is the U.S. national stage of PCT/US99/00419 filed on Jan. 8, 1999, which is based on and claims the benefit of U.S. Provisional Applications Nos. 60/071,070 filed on Jan. 9, 1998 and 60/111,531 filed on Dec. 9, 1998. Each of the foregoing applications are incorporated herein in their entirety by this reference.

This research was funded in part by Outstanding Investigator Grant CA44344-05-09 awarded by the National Cancer Institute, DHHS. The United States government may have certain rights to this invention.

The present invention relates generally to the field of compounds which may be useful in the treatment of one or more neoplastic diseases and more particularly, this invention relates to the synthesis of water soluble prodrugs of the antineoplastic compound denominated "combretastatin A-4."

FIELD OF THE INVENTION

The present invention relates to new and improved methods of synthesizing prodrugs and trans-isomers of the known antineoplastic compound denominated combretastatin A-4.

In addition, this invention teaches the chemistry of forming phosphate salts by reaction with the phenolic hydroxy group present in combretastatin A-4 and its analogs as described in U.S. Pat. Nos. 4,940,726; 5,409,953; and 5,569,786. combretastatin A-4 has poor water solubility distribution within biological systems. The elucidation and isolation of combretastatin A-4 is described in U.S. Pat. No. 4,996,237 which issued to G. R. Pettit et al., on Feb. 26, 1991, while early efforts to develop a combretastatin A-4 prodrug are described in U.S. Pat. No. 5,561,122, which issued to G. R. Pettit on Oct. 1, 1996. The general background information from each of those patents is incorporated herein by this reference thereto.

BACKGROUND OF THE INVENTION

The potent cancer cell growth and tubulin assembly inhibitor combretastatin A-4 was originally isolated from the African tree *Combretum caffrum* (*Combretaceae*) circa 1985 and has been undergoing preclinical development. However, because of the very sparing aqueous solubility behavior of the phenol and its alkali metal salts, drug formulation attempts have given unsatisfactory results. The present invention represents a breakthrough in the continuing effort to synthesize practical water soluble prodrugs based on combretastatin A-4 and is a significant advance over the early efforts described in U.S. Pat. No. 5,561,122, supra.

In certain African Zulu traditional practices, the root bark of *Combretum caffrum* (*C. salicyolium, combretaceae* Family) is used as a charm for causing harm to an enemy. Combretastatin A-4, 1a, a Z-stilbene, isolated (Pettit et al., 1989, Isolation and structure of the strong cell-growth and tubulin inhibitor combretastatin A-4, *Experimentia*, 45, 209) from this tree has been shown to be a potent cancer cell growth inhibitor (El-Zayat et al., 1993, In vitro evaluation of the antineoplastic activity of combretastatin A-4, a natural product from *Combretum caffrum* (arid shrub), *Anti-Cancer Drugs*, 4, 19); cancer anti-agent (Dark et al., 1997, combretastatin A-4, an agent that displays potent and selective toxicity towards tumour vasculature); and a tubulin assembly inhibitor (Lin et al., 1989, Antimitotic natural products combretastatin A-4 and combretastatin A-2: studies on the mechanism of their inhibition of the binding of colchicine to tubulin, *Biochemistry*, 28, 6984). Combretastatin a-4 is now in clinical development.

Although combretastatin A-4 has a phenol hydroxyl group and has demonstrated considerable promise as a unique anticancer agent, its development has been inhibited by its extremely poor solubility in water. A series of water-soluble derivatives have been recently reported (Brown et al., 1995, Synthesis of water-soluble sugar derivatives of combretastatin A-4, *Journal of the Chemical Society, Perkin Transactions I*, 577; Woods et al., 1995, The interaction with tubulin of a series of stilbenes based on combretastatin A-4, *British Journal of Cancer*, 71, 705; and, Bedford et al., 1996, Synthesis of Water-Soluble Prodrugs of the Cytotoxic Agent combretastatin A-4, *Bioorganic & Medicinal Chemistry Letters*, 6, 157) where the water-soluble phosphate sodium salt, 1 h, (Pettit et al., 1995, Antineoplastic agents 322, Synthesis of combretastatin A-4 prodrugs, *Anti-Cancer Drug Deign*, 10, 299; and, Pettit, U.S. Pat. No. 5,561,122) proved to be the most attractive. However, the phosphorylation sequence employing bis(2,2,2-trichloroethyl)phosphoro-chloridate, subsequent reduction (Zn, $CH_3CO_2H$), and isolation by ion-exchange chromatography was not well suited to producing prodrug 1 h on a large scale and as such, posed a significant economic obstacle to its ultimate commercialization.

While prodrug options are steadily increasing and include poly(ethylene glycol) esters (Greenwald et al., 1996, Drug delivery systems: water soluble taxol 2'-poly(ethylene glycol) ester prodrugs-design and in vivo effectiveness, *The Journal of Medicinal Chemistry*, 39, 424); quaternary salts (Lackey et al., 1996, Water soluble inhibitors of topoisomerase I: quaternary salt derivatives of camptothecin, *The Journal of Medicinal Chemistry*, 39, 713); sulfonate salts (Hejchman et al., 1995, Synthesis and cytotoxicity of water-soluble ambrosin prodrug candidates, *The Journal of Medicinal Chemistry*, 38,3407); urethans (Izawa et al., 1995, Design and synthesis of an antitumor prodrug released by the reaction with sulfhydryl compounds, *Bioorganic & Medicinal Chemistry Letters*, 5, 593); biodegradable polymers (Gombotz et al., 1995, Biodegradable polymers for protein and peptide drug delivery, *Bioconjugate Chemistry*, 6, 332); and, a variety of other methods (Jungheim et al., 1994, Design of antitumor prodrugs: substrates for antibody targeted enzymes, *Chemical Reviews*, 94, 1553), the present disclosure is focused on the previously introduced sodium phosphate derivative 1h (which is equivalent to the sodium phosphate derivative 3d, produced by the methods set forth herein, see below) of combretastatin A-4. From evidence at hand phosphate 1h (as well as 3d) is presumed to be appropriately dephosphorylated by serum phosphatases and then transported intracellularly.

Furthermore, the phosphate prodrug approach has proved useful with substances as diverse as Etoposide (Saulnier ea al., 1994, Synthesis of etoposide phosphate, BMY-40481: a water-soluble clinically active prodrug of etoposide, *Bioorganic & Medicinal Chemistry Letters*, 4, 2567); Taxol (Mamber et al., 1995, Tubulin polymerization by paclitaxel (Taxol) phosphate prodrugs after metabolic activation with alkaline phosphatase, *The Journal of Pharmacology and Experimental Therapeutics*,374, 877; Ueda et al., 1995, Novel, water-soluble phosphate derivatives of 2'-ethoxycarbonylpaclitaxel as potential prodrugs of paclitaxel: synthesis and antitumor evaluation, *Bioorganic & Medicinal Chemistry Letters*, 5, 247; and Ueda, et al., 1993, Novel water soluble phosphate prodrugs of Taxol possessing in vivo antitumor activity, *Bioorganic & Medicinal Chemistry Letters*, 3, 1761); and tyrosine-containing peptides (Chao et al., 1993, N,N-Diisopropyl-bis [2-(trimethylsily)ethyl]phosphoramidite, An attractive phosphorylating agent compatible with the Fmoc/t-butyl strategy for the synthesis of phosphotyrosine containing peptides, *Tetrahedron Letters*, 34, 3377). As shown herein below for prodrug 1 h (also, 3d), phosphate ester salts are generally cleaved in vivo (Bundgaard (ed.), 1985, Design of prodrugs, pp. 1-92, Elsevier: New York) and are stable enough to usually allow formulation into solutions with practical shelf lives (Flynn et al., 1970, Factors influencing solvolysis of corticosteroid-21-phosphate esters, *Journal of Pharmaceutical Sciences*, 59, 1433). To improve the synthetic scaleup practicality for the sodium phosphate ester prodrug 1 h (3d) of combretastatin A-4, three new phosphate esters have been synthesized which were easily transformed into the water-soluble prodrug 3d as is herein described.

The aggressive behavior of a broad spectrum of human cancer types such as breast carcinoma is related to the facility for rapid tumor angiogenesis. Neovascularization represents a very attractive target for new tumor antiangiogenesis-type anticancer drugs. Combretastatin A-4 1a was found to show potent antiangiogenesis activity and the derived sodium phosphate prodrug 1h (3d) is a powerful in vivo inhibitor of tumor vascularization. Currently prodrug 1h is in clinical development. A practical synthetic procedure for providing the pure drug in quantity for clinical trials has continued to be an important research objective. As described, the present invention is predicated upon the discovery of a considerably improved sequence utilizing in situ prepared dibenzyl chlorophosphite for phosphorylating phenol 1a, cleavage of the benzyl ester groups by trimethyliodosilane and treatment of the product with sodium methoxide to afford prodrug 1h (herein 3d) in good yield. However, the product was found to be accompanied by an isomeric substance that was first revealed by the appearance of some opalescence in aqueous solutions of prodrug 3d. The side product was believed to be the corresponding trans-stilbene 4c and was eliminated by extraction and fractional recrystallization. The purity of prodrug 3d was readily assigned by an ion-pair HPLC analysis using a phosphate buffer.

This further study was focused on confirming the structure of the persistent by-product (assumed to be 4c) by synthesis. In addition, the evaluation-of combretastatin A-4 prodrugs was extended by preparing an extended series of phosphate metal and ammonium cation derivatives of the phosphoric acid precursor of prodrug 3d. Synthesis of the trans-stilbene phosphate 4c was also considered potentially useful for SAR purposes in view of the chemopreventative activities of certain trans-stilbene phenols such as resveratrol.

Combretastatin A-4 is essentially insoluble in water. This characteristic has significantly interfered with accomplishing the necessary formulations of pharmaceutical preparations of this compound for use in pre-clinical development. Hence, derivatives of the combretastatin A-4, 1a, 3' phenol group were prepared for evaluation as possible water soluble prodrugs. As noted in U.S. Pat. No. 5,561,122, the sodium salt 1b, potassium salt 1c and hemisuccinic acid ester 1d derivatives of phenol 1a were essentially insoluble in water. Indeed, these substances regenerated combretastatin A-4 upon reaction with water. A series of other simple derivatives proved unsatisfactory in terms of water solubility or stability or both. The most soluble derivatives evaluated included the ammonium 1f, potassium 1 g and sodium 1h phosphate salts where the latter two proved most stable and suitable. Both the sodium and other phosphate salt derivatives of combretastatin A-4 described herein were also found to exhibit the requisite biological properties necessary for a useful prodrug.

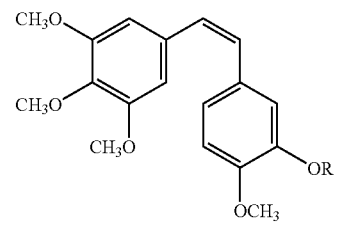

1a, R = H
b, R = Na
c, R = K
d, R = COCH$_2$CH$_2$CO$_2$H

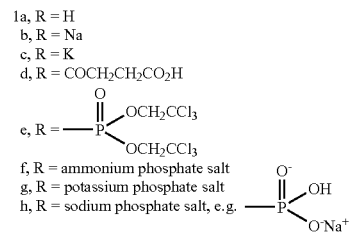

f, R = ammonium phosphate salt
g, R = potassium phosphate salt
h, R = sodium phosphate salt, e.g.

SUMMARY OF THE INVENTION

Combretastatin A-4 1a, as the phosphate ester prodrug 1h (and, hereinafter 3d) is a potent antineoplastic and antiangiogenesis substance and is in clinical development. For the purpose of improving the phosphorylation synthetic sequence from combretastatin A-4, new routes were investigated. The phosphorylation step was found to be considerably improved using in-situ generated dibenzyl chlorophosphite. Cleavage of the benzyl esters employing a trimethylchlorosilane/sodium iodide procedure, followed by treatment with sodium methoxide, led to the water-soluble prodrug 3d in high yield.

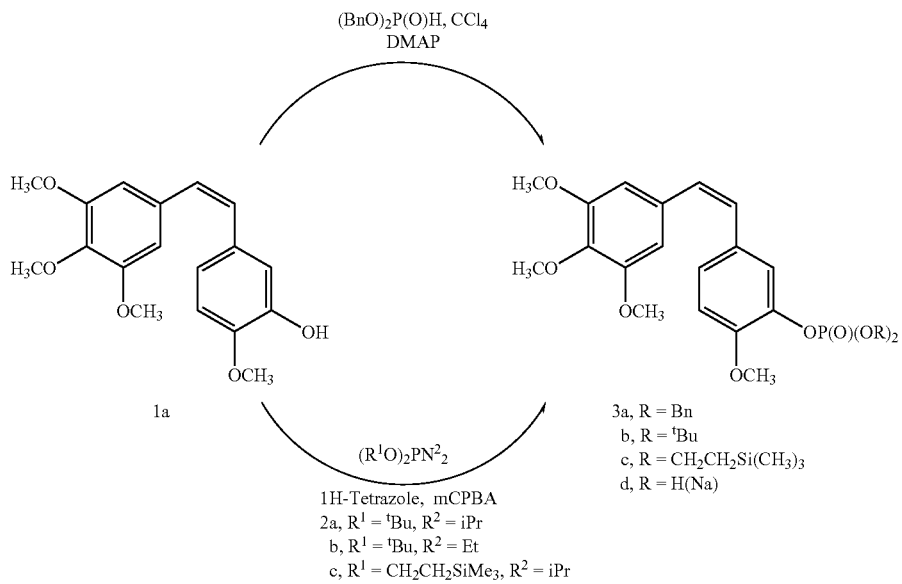

As shown more particularly above for prodrug 3d, phosphate ester salts are generally cleaved in vivo (Bundgaard, supra). To improve the synthetic scaleup practicality for the sodium phosphate ester prodrug of combretastatin A-4, three new phosphate esters 3a, 3b, and 3c have been synthesized the latter of which was easily transformed into the water-soluble prodrug 3d as is described in more detail below.

The (E)-stilbene isomer 4c (see below) of the natural (Z)-combretastatin A-4 prodrug 3d was also efficiently prepared from (E)-combretastatin A-4 1a by an analogous reaction sequence employing phosphorylation (dibenzyl chlorophosphite), cleavage (trimethyliodosilane) of the benzyl ester and reaction of the resulting phosphoric acid with sodium methoxide. The sodium phosphate product 4c was found to be an important side-product, presumably from iodine-catalyzed isomerization, when this synthetic route was used to obtain the combretastatin A-4 prodrug 3d.

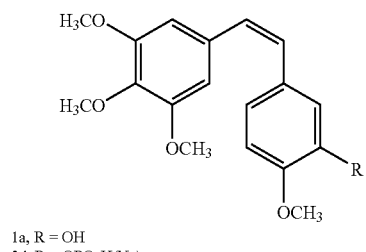

1a, R = OH
3d, R = OPO$_3$H(Na)

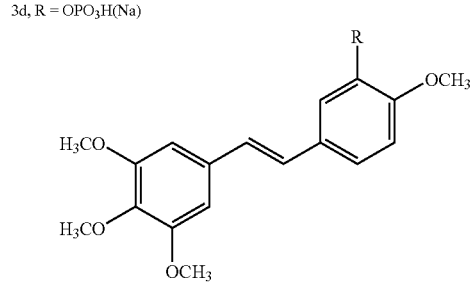

4a, R = OH
b, R = OPO$_3$Bn$_2$
c, R = OPO$_3$H(Na)

The phosphoric acid precursor of prodrug 3d derived from (Z)-combretastatin A-4 1a was also converted to a series of metal cation and ammonium cation salts to evaluate effects on human cancer cell growth, antimicrobial activities and solubility behavior. Thus, several new combretastatin A-4 prodrug modifications 5a-s (see below) have been prepared and found to exhibit inhibitory action against various bacteria and opportunistic fungi.

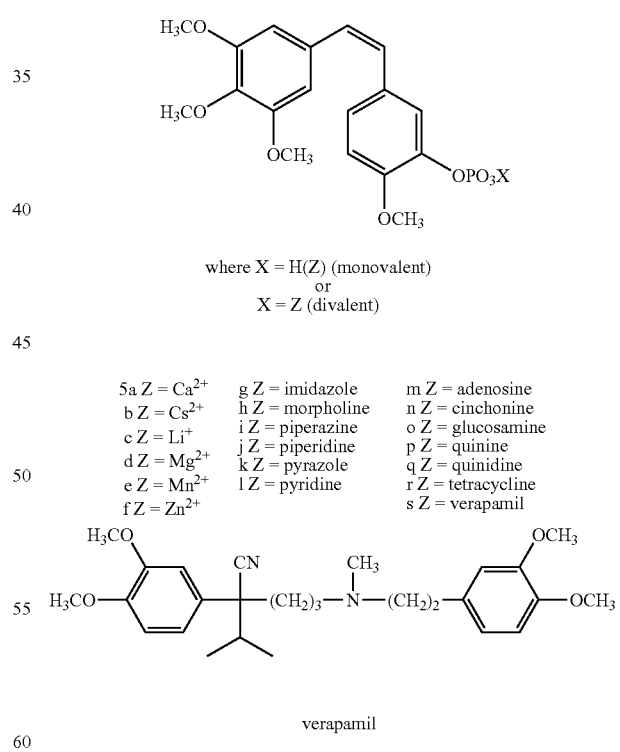

where X = H(Z) (monovalent)
or
X = Z (divalent)

5a Z = Ca$^{2+}$       g Z = imidazole      m Z = adenosine
b Z = Cs$^{2+}$        h Z = morpholine     n Z = cinchonine
c Z = Li$^+$           i Z = piperazine     o Z = glucosamine
d Z = Mg$^{2+}$        j Z = piperidine     p Z = quinine
e Z = Mn$^{2+}$        k Z = pyrazole       q Z = quinidine
f Z = Zn$^{2+}$        l Z = pyridine       r Z = tetracycline
                                            s Z = verapamil verapamil Accordingly, the prime object of the subject invention is to prepare prodrugs of combretastatin A-4 which are both water soluble and stable, as well as to improve the means of synthesizing such compounds.

These and still further objects as shall hereinafter appear are readily fulfilled by the present invention in a remarkably unexpected manner as will be readily discerned from the following detailed description of an exemplary embodiment thereof especially when read in conjunction with the structures set forth above and the accompanying drawing.

BRIEF DESCRIPTION OF THE DRAWINGS

FIG. 1 comprises high performance liquid chromatography charts for a) mixture of (Z)- and (E)-combretastatin A-4 prodrugs b) combretastatin A-4 prodrug, 100% pure by HPLC.

DETAILED DESCRIPTION OF THE INVENTION

The process by which combretastatin may be synthesized is well known in the art. See, Pettit et al., Isolation and structure of the strong cell growth and tubulin inhibitor combretastatin A-4, *Experimentia*, 209 (1989), supra. Combretastatin A-4, synthesized by that method disclosed in U.S. Pat. No. 4,996,237 ("the '237 patent"), was used throughout this process.

Combretastatin A-4 (1a) was synthesized as previously described by Pettit et al., in 1995. Diisopropylethylamine (98%), lithium hydroxide monohydrate, cesium hydroxide, zinc acetate dihydrate, quinine monohydrate, piperidine, pyrazole, and sodium methoxide (95%), dibenzyl phosphite, 4-dimethylaminopyridine (DMAP), 1H-Tetrazole (98%), 85% 3-chloroperoxybenzoic acid (m-CPBA), chlorotrimethylsilane (98%), trifluoroacetic acid (99%), triethylamine, and sodium methoxide (95%) were obtained from Sigma-Aldrich Chemical Company. The tert-butanol was obtained from Acros Organics. Calcium acetate, magnesium acetate tetrahydrate, manganese acetate and other reaction and isolation reagents were obtained from the Baker Chemical Company. Tetrahydrofuran was distilled from sodium/benzophenone. Imidazole was recrystallized from n-hexane, and piperazine was recrystallized from ethanol and dried in vacuo. The morpholine was dried with KOH and then fractionally distilled; pyridine was dried over $CaH_2$ and fractionally distilled, then stored over KOH. Adenosine was obtained from Nutritional Biochemicals Corporation; cinchonine, from Mateson, Cole & Bell and was recrystallized from ethanol prior to use; D-glucosamine was from Nutritional Biochemicals Corporation; quinidine, was from J. T. Baker; tetracycline, from Mateson, Cole & Bell; and verapamil, from the Alexis Corporation. "Ether", refers to diethyl ether. All solvents were redistilled prior to use. The 1.0 M solutions of the metal salts were in distilled water, and the 1.0 M solutions of the amines were in dry methanol. The di-tert-butyloxy(N,N-diethylamido)phosphine was prepared as previously described by Johns et al (1988, Di-tert-butyl N,N-Diethylphosphoramidite, A New Phosphitylating Agent for the Efficient Phosphorylation of Alcohols, *Synthesis*, pp. 142-144).

Reactions were monitored by thin-layer chromatography using ANALTECH silica gel GHLF Uniplates visualized under long-wave and short-wave UV irradiation. Solvent extracts of aqueous solutions were dried over anhydrous sodium sulfate. Where appropriate, the crude products were separated by flash column chromatography (230-400 mesh ASTM) from E. Merck.

Melting points were measured with an ELECTROTHERMAL digital melting point apparatus, model IA9200, and are uncorrected. The IR spectra were obtained using a NICOLET FTIR Model MX-1 instrument. EIMS data was recorded with a MAT 312 mass spectrometer, and high-resolution FAB spectra were obtained with a KRATOS MS-50 mass spectrometer (Midwest Center for Mass Spectrometry, University of Nebraska, Lincoln, Nebr.). All $^1$H- and $^{13}$C-NMR spectra were obtained using a VARIAN GEMINI 300 MHz instrument with $CDCl_3$ (TMS internal reference) as solvent unless otherwise noted. The $^{31}$P-NMR spectra were obtained in $CDCl_3$ with 85% $H_3PO_4$ as an external standard employing a UNITY 500 MHz instrument. Elemental analyses were determined by Galbraith Laboratories, Inc., Knoxville, Tenn.

HPLC Separations and Analysis

HPLC analyses were performed on a HEWLETT-PACKARD HP 1050 Series 3D CHEMSTATION, Rev. A.03.01, liquid chromatograph. All solvents used were HPLC grade and filtered before use. HPLC separation and analysis procedures were based on aqueous buffered ion-pair reverse-phase gradient elution at 33° C. Flow rate: 1.2 ml/min. Column: MERK LICHROSPHERE 100 RP 18 (5 µm), 250×4.0 mm (LICHROCART 250-4). Eluents: Eluent A. 5 mM tetrabutylammonium hydrogen sulfate, 5 mM $H_3PO_4$, 5 mM $KH_2PO_4$. Eluent B. 75% $CH_3CN$. Gradient: a) Hold 4 minutes at 65% A, 35% B, b) 8 minutes linear gradient, 65% A to 10% A, c) Hold 3 minutes. Detector: 310 nm UV.

di-tert-Butyoxy(N,N-diisopropylamide)phosphine (2a)

A solution of tert-butanol (3.7 g, 4.7 ml, 50 mmol, 2.0 equiv) and triethylamine (5.6 g, 7.7 ml, 55 mmol, 2.2 equiv) in dry ether (20 ml) was added to dichloro-N,N-diisopropylphosphine (5.0 g, 25 mmol) in dry ether (5 ml) while maintaining the solution temperature below 0° C. Upon completion of addition (about 15 minutes), the solution was allowed to warm to room temperature and stirred for a further 3 hours. A solution of 5% aqueous sodium bicarbonate (10 ml) was added, the aqueous phase was removed, and the ethereal solution was washed with 5% aq. sodium bicarbonate (2×10 ml), saturated aq. NaCl (25 ml), dried, filtered, and solvent removed to give a clear residual oil. Purification by vacuum distillation gave the product as a clear oil (4.3 g, 63%). b.p. 56-57° C./0.05 mm Hg; $^1$H-NMR (300 MHz) δ 1.17 (d, J=6.0 Hz, $CH(CH_3)_2$), 1.35 (s, 18H, 2×$(CH_3)_3C$), 3.53-3.68 (m, 2×$(CH_3)_2CH$); $^{13}$C-NMR (125 MHz) δ 24.21 (d, $J_{PC}$=7.73 Hz), 31.06 (d, $J_{PC}$=9.75 Hz), 43.09 (d, $J_{PC}$=13.88 Hz), 74.50 (d, $J_{PC}$=9.75 Hz); $^{31}$P-NMR (202 MHz) δ 130.0 (s).

di-tert-Butyloxy(N,N-diethylamido)phosphine (2b)

Phosphine 2b was as previously described (Johns et al, 1988, supra): b.p. 49-51° C./0.005 mm Hg (55% yield); $^1$H-NMR (300 MHz) δ 1.06 (t, 6H, $J_{HH}$=7.8 Hz), 1.33 (s, 18H, $C(CH_3)_3$), 3.03 (dq, 4H, $J_{HH}$=7.8 Hz, $J_{PH}$=9.0 Hz, $PCH_2CH_3$); $^{13}$C-NMR (75 MHz) δ 14.84 (d, $J_{PC}$=3.9 Hz), 30.88 (d, $J_{PC}$=9.75 Hz), 37.45 (d, $J_{PC}$=21.3 Hz), 74.40 (d, $J_{PC}$=11.63 Hz).

Bis-[2-(trimethylsily)ethoxy]-N,N-diisopropylamidophosphine (2c)

A solution of 2-(trimethylsilyl)ethanol (1.2 g, 9.9 mmol, 2 equiv) and triethylamine (1.5 ml, 10.9 mmol, 2.2 equiv) in dry ether (10 ml) was added to dichloro-N,N-diisopropylamidophosphine (1.0 g, 4.9 mmol) in dry ether (10 ml) and the temperature was maintained below 0° C. Upon completion of addition (ca 30 min), the mixture was allowed to warm to room temperature and stirring continued for 3 hours. After adding a solution of 5% aq. $NaHCO_3$ (10 ml) the aqueous phase was washed with 5% aq. $NaHCO_3$ (2×10 ml), saturated aq NaCl (10 ml), dried and filtered. Removal of solvent in vacuo afforded a clear oil (2.2 g, 78%). Purification by vacuum distillation gave the product as a clear oil.

b.p. 62-64° C./0.005 mm; IR (neat) $v_{max}$ 2960 (s), 2897 (m), 1462 (w), 1396 (m), 1363 (m), 1249 (s), 1186 (s), 1126 (m) 1045 (s), 972 (s), 837 (s), 744 (s), 694 (s), 663 (w) cm$^{-1}$; $^1$H-NMR (300 MHz) δ 0.00 (s, 18H), 1.02 (m, 4H) 1.16 (d, J=6.6 Hz, 12H), 3.52-3.77 (m, 6H); $^{13}$C-NMR (75 MHz) δ -1.49, 20.00, 24.41, 24.51, 42.47, 42.63, 60.43, 60.67; $^{31}$P-NMR (202 MHz) δ 143.50.

3'-O-Bis(benzyl)phosphorylcombretastatin A-4 (3a)

A flame-dried, 3-neck flask containing a teflon stirbar was fitted with a septa, thermometer, and argon inlet. The phenol (1a, 20.0 g, 63.2 mmol) was dissolved in acetonitrile (200 ml) with stirring and then cooled to -25° C. Carbon tetrachloride (30.5 ml, 316 mmol, 5 equiv) was added and the solution stirred for 5 minutes. Diisopropylethylamine (23.13 ml, 133 mmol, 2.1 equiv) was added via syringe, followed by DMAP (772 mg, 6.32 mmol, 0.1 equiv). One minute later dropwise (slow) addition of dibenzyl phosphite (20.33 ml, 92 mmol, 1.45 equiv) was begun at such a rate that the reaction temperature was kept below -10° C. When the reaction was complete (1 hr by TLC analysis) 0.5 M aqueous $KH_2PO_4$ was added (50 ml) and the solution allowed to warm to room temperature. After extraction with ethyl acetate (3×100 ml), the combined solvent extract was washed with water (100 ml), saturated NaCl (100 ml) and dried. Filtration and removal of solvent under reduced pressure gave a faint yellow oil. The oily residue was chromatographed on a column of silica gel (hexane-ethyl acetate, 3:2) to give a clear oil which crystallized from ethyl acetate-hexane to give pure, colorless needles (36.0 g; 98%): m.p. 73° C.; $R_f$ 0.26 (hexane-ethyl acetate, 3:2); EIMS m/z 576 (100, M$^+$), 561 (8), 485 (2), 394 (2), 378 (3), 363 (3), 252 (5), 181 (3); IR (neat) $v_{max}$ 3005, 2939, 2837, 1579, 1512, 1454, 1425, 1280, 1240, 1122, 1010, 891, 740, 698 cm$^{-1}$; $^1$H-NMR (300 MHz) δ 3.67 (s, 6H, 2×OCH$_3$), 377 (s, 3H, OCH$_3$), 3.80 (s, 3H, OCH$_3$), 5.12 (s, 2H, CH$_2$—Ar), 5.14 (s, 2H, CH$_2$—Ar), 6.40 (d, J=12.0 Hz, 1H), 6.45 (d, J=12.0 Hz, 1H), 6.48 (s, 2H), 6.78 (d, J=9.0 Hz, 1H), 7.06 (dd, J=9.0, 1.8 Hz, 1H), 7.15 (d, J=1.8 Hz, 1H), 7.31 (s, 10H, Ar—H); $^{13}$C-NMR (75 MHz) δ 152.97, 139.32, 139.22, 135.67, 132.46, 130.19, 129.67, 128.53, 127.88, 126.56, 122.21, 112.27, 105.93, 69.79, 69.72, 60.86, 60.40, 55.92, 21.05, 14.22; $^{31}$P-NMR (202 MHz) δ -5.29; Anal. Calcd. for $C_{32}H_{33}O_8P$: C, 66.67; H, 5.77. Found: C, 66.96; H, 6.05.

3'-O-Bis(tert-butyl)phosphorylcombretastatin A-4 (3b)

Method A. 1H-Tetrazole (3.73 g, 53 mmol, 3.67 equiv) was added in one portion to a stirred solution of combretastatin A-4 (1a, 5.00 g, 16 mmol, 1.0 equiv) and di-tert-butyloxy-N,N-diethylamidophosphine (5.19 g, 21 mmol, 1.3 equiv) in dry tetrahydrofuran (15 ml). The solution was stirred under argon for 20 minutes at room temperature and cooled to -70° C. (CO$_2$/acetone). Next a solution of 85% m-CPBA (3.22 g, 19.0 mmol) in dry dichloromethane (10 ml) was added (rapidly) such that the reaction mixture temperature was kept below -30° C. After stirring for 5 min at room temperature, 10% aqueous sodium bicarbonate (15 ml) was added. The solution was stirred for another 10 minutes and extracted with ether (70 ml). The ethereal phase was washed with 10% aq. sodium bicarbonate (2×20 ml), 1N NaOH (6×40 ml), dried and filtered. Evaporation of solvent under reduced pressure gave a yellow oil which was purified by flash column chromatography (silica gel; 3:2 hexane-ethyl acetate) to give the title compound as a clear oil (1.15 g; 75%): $R_f$ 0.25 (hexane-ethyl acetate, 3:2); EIMS m/z 508 (M$^+$, 22), 452 (5), 437 (7), 396 (100), 381 (17), 364 (4), 349 (3), 316 (5); IR (neat) $v_{max}$ 3462, 2980, 2937, 2837, 2243, 1579, 1512, 1462, 1425, 1371, 1327, 1276, 1174, 1128, 999, 920, 868, 731, 646 cm$^{-1}$; $^1$H-NMR (300 MHz) δ 1.47 (s, 18H, 2×C(CH$_3$)$_3$), 3.69 (s, 6H, 2×OCH$_3$), 3.82 (s, 3H, OCH$_3$), 3.83 (s, 3H, OCH$_3$), 6.42 (d, J=12 Hz, 1H), 6.47 (d, J=12 Hz, 1H), 6.51 (s, 2H, 2,6-H), 6.79 (d, J=8.5 Hz, 1H), 7.03 (dd, J=8.5, 1.8 Hz, 1H), 7.31 (d, J=1.8 Hz, 1H); $^{13}$C-NMR (75 MHz) δ 152.94, 132.62, 129.85, 129.25, 129.02, 125.63, 121.80, 112.14, 105.93, 99.28, 83.49, 60.89, 55.92, 29.80, 29.72; $^{31}$P-NMR (202 MHz, CDCl$_3$/85% H$_3$PO$_4$) δ -14.47; Anal. calcd. for $C_{26}H_{37}O_8P$: C, 61.40%; H, 7.33%. Found: C, 60.92; H, 7.67.

Method B: The same procedure as in Method A above was followed except di-tert-butyloxy-N,N-diisopropylamidophosphine was used as the phosphorylating agent. Yield: 78%.

3'-O-Bis(trimethylsilylethoxy)phosphorylcombretastatin A-4 (3c)

The same procedure as in Method A above was used, with bis-[2-(trimethylsily) ethoxy-N,N-diisopropylamidophosphine (2c), giving the product as a colorless oil (8.67 g, 91%): $R_f$ 0.26 (hexane-ethyl acetate, 3:1); EIMS m/z 596 (M$^+$, 90), 568 (20), 540 (21), 525 (38), 496 (10), 468 (40), 453 (13), 396 (22), 283 (10), 252 (11), 211 (13), 147 (15), 73 (100); IR (neat) $v_{max}$ 2999, 2955, 2901, 2837, 1579, 1512, 1464, 1525, 1276, 1249, 1217, 1180, 1128, 991, 856, 767, 696 cm$^{-1}$; $^1$H-NMR (500 MHz) δ 0.00 (s, 18H), 1.04 (m, 4H, —CH$_2$Si—), 3.63 (s, 6H, 2×OCH$_3$), 3.77 (s, 6H, 2×OCH$_3$), 4.17 (m, 4H, —OCH$_2$CH$_2$—), 6.09 (s, 2H), 6.42 (d, J=12.5 Hz, 1H), 6.47 (d, J=12.5 Hz, 1H), 6.77 (d, J=8.5 Hz, 1H), 7.03 (dd, J=8.5, 1.0 Hz, 1H), 7.21 (d, J=1.0 Hz, 1h); $^{13}$C-NMR (75 MHz) δ 152.77, 149.69, 139.54, 137.05, 132.24, 129.94, 129.37, 128.41, 126.05, 121.78, 112.08, 105.76, 66.72, 64.00, 60.59, 55.70, 19.51, 19.20, -1.72; $^{31}$P-NMR (202 MHz) δ -5.54.

Sodium (Z)-combretastatin A-4 3'-O-phosphate (3d)

Procedure A. To a solution of the benzyl ester (3c, 20.5 g, 35.6 mmol) and sodium iodide (10.7 g, 71 mmol, 2 equiv) in dry acetonitrile (100 ml, in a flame-dried flask under argon) was slowly added chlorotrimethylsilane (9.02 ml, 71 mmol, 2 equiv) with vigorous stirring. The reaction mixture was stirred for 20 minutes at which point TLC analysis (hexane-ethyl acetate, 3:2) showed no starting material. Water (just enough to dissolve the salts) was added and the straw color removed by the addition of 10% aq.sodium thiosulfate (2 ml). The organic phase was separated and the aqueous phase extracted with ethyl acetate (4×50 ml). The combined extract was concentrated in vacuo to give a pale yellow foam. The foam was dissolved in dry methanol (100 ml) and sodium methoxide (95%, 4.1 g, 71 mmol, 2 equiv) was added in one portion and the solution stirred for 9 hours. The methanol was removed in vacuo and the solid recrystallized from water-acetone and methanol-acetone to give colorless crystals (14 g, 90%): m.p. 190-195° C. (decomp); $R_f$ 0.64 (n-butanol-methanol-water-ammonia, 4:3:2:1); UV $\lambda_{max}$ (log ε) in CH$_3$OH, 200 (4.54), 278 (4.25) nm (4.54), 196 (4.48) nm; IR (KBr) $v_{max}$ 2941 m, 2839s, 2361m (broad), 1581s, 1514s, 1431m, 1240m, 1124s, 983m, cm$^{-1}$; $^1$H-NMR (500 MHz, D$_2$O) δ 3.50 (s, 6H, 3,5-OCH$_3$), 3.57 (s, 3H, 4'-OCH$_3$), 3.68 (s, 3H, 4-OCH$_3$), 6.26 (d, 1H, J=12.5 Hz, H-1a'), 6.42 (s, 2H, H-2,6), 6.44 (d, 1H, J=12.5 Hz, H-1a), 6.63 (d, 1H, J=8.5 Hz, H-5'), 6.71 (dd, 1H, J=2, 8.5 Hz, H-6'), 7.19 (d, 1H, J=2 Hz, H-2'); $^{13}$C-NMR (125 MHz, D$_2$O) δ 153.17, 150.50, 143.40, 136.90, 134.65, 131.28, 130.97, 129.93, 124.69, 122.64, 113.58, 107.54, 61.97, 57.10, 56.90; HRFAB m/z 441.06942 [M+Na]$^+$, 419 [M+H], 396 [M−Na+H]$^+$. calc. 441.06912 for $C_{18}H_{20}O_8PNa_2$, anal.

Na, 5.04%, H$_2$O 6.26% calc. for C$_{18}$H$_{20}$O$_8$PNa·1½ H$_2$O hydrate, Na 5.16%, H$_2$O 6.07%.

Sodium phosphate 3d prepared by Procedure A was identical (TLC and spectra) with an earlier specimen (1h, Pettit et al., 1995,supra; and U.S. Pat. No. 5,561,122) obtained by the initial 3'-O-bis(2,2,2-trichloroethyl)phosphoryl route and exhibited solubility in distilled water of >20 mg/ml at 25° C.

Procedure B: A mixture of the di-tert-butylphosphoryl ester 3b (7.25 g) and trifluoroacetic acid (25 ml) in dry dichloromethane (25 ml) was stirred at ambient temperature for 45 minutes (cleavage complete by TLC analysis hexane-acetone, 3:1). Water (10 ml) was added and solvent evaporated. Residual TFA was removed azeotropically with toluene (3×20 ml), and the resulting oily residue was dried under vacuum (0.005 mm/Hg) for 1 hour. The oil was dissolved in dry methanol (2 ml) and sodium methoxide (1.60 g, 28 mmol, 2.0 equiv) was added. The solution was stirred under argon for 14 hours, solvent was removed in vacuo and the remaining solid dried. The residue was dissolved in water (10 ml) and the solution filtered through a fine porosity sintered glass funnel. Concentration of the filtrate gave a white solid which recrystallized from water-acetone to give a colorless powder (5.8 g, 92%) identical with the sample of prodrug 3d prepared by Procedure A.

Procedure C: Tetrabutylammonium fluoride (8.38 ml, 1.0 M in THF; 8.38 mmol) was slowly added employing a syringe to a stirred (under nitrogen) solution of di-silyl ethoxyphosphoryl ester 3c (5.0 g, 8.38 mmol) in 15 ml of anhydrous tetrahydrofuran. After 30 minutes, TLC analysis (hexane-ethyl acetate, 3:2) indicated the reaction was complete. Ice (5 g) was added, followed by ether (50 ml). The organic solvent was separated, washed with water (3×50 ml), dried, filtered and solvent removed in vacuo to yield a straw colored gum. The product was dissolved in methanol (5 ml) and sodium methoxide (0.90 g, 16.8 mmol, 2 equiv) was added. The solution was stirred under argon for 12 hours, solvent was removed under reduced pressure and the residual solid was recrystallized from water-acetone to give a colorless powder (3d, 3.60, 98%) identical with the product from Procedure A.

After completing the first synthesis of sodium combretastatin A-4,3'-O-phosphate 3d a number of other phosphorylation approaches were explored toward the objective of establishing a procedure more readily adapted to large scale synthesis. Selection of an appropriate method for phosphorylation of combretastatin A-4 1a was also limited by available methods for removal of the eventual phosphate protecting groups. An alternative dibenzylphosphite-carbon tetrachloride procedure proved very practical for obtaining phosphate ester 3a in high yield (95%). Catalytic hydrogenolysis of the benzyl oxygen bonds under varied conditions gave a concomitant reduction of the olefin bridge. Other benzyl oxygen cleavage methods investigated included the use of triphenylcarbonium tetrafluoroborate, arylthiotrimethylsilane-zinciodide, acidic alumina in a microwave and the Lewis acid SnCl$_4$ (Mukai et al., 1996, Studies on the total synthesis of antitumor styryllactones: stereoselective total syntheses of (+)-goniofufurone, (+)-goniobutenolide A, and (−)-goniobutenolide B, *Tetrahedron*, 52, 6547). While all cleaved the benzyl group, they appeared (by TLC) to cause varying levels of cis→trans isomerism. Finally, it was determined that trimethylsilyl iodine, neat or generated in-situ, provided the best route to obtain the corresponding phosphoric acid. Treatment of the latter with sodium methoxide gave, following recrystallization, a high overall yield of phosphate salt 3d.

The second series of phosphorylating agents studied were the various alkylamidophosphines which have been shown to readily phosphorylate alcohols and phenols in high yield. Di-tert-butyloxy(N,N-diisopropylamido)phosphine 2a, was prepared in good yield from dichloro(N,N-diisopropylamido)phosphine and tert-butanol. Phosphines 2b and 2c were prepared in a similar manner by reacting dichloro(N, N-diethylamido)phosphine and dichloro(N,N-diisopropylamido)phosphine with tert-butanol and 2-(trimethylsilyl) ethanol, respectively. In the presence of the catalyst, 1H-tetrazole, these reactive amides nicely phosphorylated phenol 1a to give the corresponding phosphate esters 3b and 3c in greater than 90% yields. Cleavage of the ester protecting groups was easily affected with either trifluoroacetic acid for the tert-butyl ester or tetrabutylammonium fluoride for the bis(2-trimethylsilyl)ethyl ester. After isolation, the phosphoric acid derivative was treated with sodium methoxide in methanol to afford sodium phosphate 3d in high yield.

The three new phosphorylation routes to prodrug 3d, described herein, were readily employed to obtain 10 g or greater amounts without any decrease in yields or purity. The resulting phosphate prodrug 3d samples proved to be identical with our original specimen and therefore the clinical supply requirements for combretastatin A-4 prodrug 3d can now be met.

Comparison of the synthetic trans-stilbene phosphate 4c (see below) with the impurity accompanying the scaleup synthesis of combretastatin A-4 prodrug 3d confirmed the structural assignment. The ion-pair HPLC analysis noted above proved to be quite useful for detecting small quantities of this impurity. Apparently the trans-stilbene 4c arose in inconsistent amounts by an electrophilic bimolecular addition of iodine to form an iodonium ion and subsequent anti-addition product (Hassner et al., 1970, Stereochemistry of halogen azide additions to olefins, The stability of three-membered iodonium vs bromonium ions, *Journal of the American Chemical Society*,92, 4879; Robertson et al., 1950, The kinetics of halogen addition to unsaturated compounds, Part XVIII, Iodine addition, *Journal of the Chemical Society*, 2191; Zanger et al., 1975, A nuclear magnetic resonance investigation of the iodination of 1,2-disubstituted ethylenes, Evidence for a trans addition—cis elimination, *Journal of Organic Chemistry*,40, 248; Ayres et al., 1971, Reaction of iodine with olefins, Kinetics and mechanism of iodine addition to pentene isomers, *Journal of the American Chemical Society*,93, 1389; Skell et al., 1964, Stereospecific trans photoaddition of elementary iodine to aliphatic olefins, Bridged iodoalkyl radicals, *Journal of the American Chemical Society*,86, 2956). Fortunately, isomeric stilbenes 3d and 4c have distinctive HPLC retention times in the phosphate buffer employed. The combretastatin A-4 prodrug 3d eluted at 9.28 minutes with UV $\lambda_{max}$ 290 nm and the trans-isomer at 9.40 minutes with UV $\lambda_{max}$ 325 nm (see Fig 1*a*-1*d*). Because the trans-isomer phosphate salt 4c proved to be sparingly soluble in water, it was simply removed from the cis-isomer phosphate salt 3d by redissolving the combretastatin A-4 prodrug 3d in a minimal amount of water and extracting with ethyl acetate. The (E)-stilbene 4c, owing to its low solubility in water, partitioned selectively into the ethyl acetate. The water phase containing the (Z)-stilbene was concentrated and the residue recrystallized from water-acetone and methanol-acetone to give the 99+% pure (by HPLC) sodium combretastatin A-4 phosphate 3d in >80% yields.

Since combretastatin A-4 binds tubulin very strongly in the colchicine binding site (Lin et al., 1988, Interactions of tubulin with potent natural and synthetic analogs of the antimitotic agent combretastatin, a structure-activity study, *Molecular Pharmacology*,34, 200), with inhibition to 97% reported, it became important to replace the sodium cations in prodrug 3d with different cations, both divalent and monovalent, in order to examine their effects on activity and solubility. Using this same approach, the sodium ions were replaced with metal cations and a variety of ammonium cations in order to examine their possible effects on the cancer cell line and antimicrobial activities and solubility. Some of these ammonium cations were explored for the purpose of possibly obtaining a stable, water-soluble drug with the ability to reverse multi-drug resistance through interference with the p-glycoprotein mechanism. Watanabe et al., 1997, *J. Nat. Cancer Inst.*, 89(7), pp. 512-518; Adams et al., 1995 *Investigational New Drugs* 13:13-21; Sato et al., 1995, *Cancer Chemother. Pharmcol.*, 35:271-277; Genne et al., 1995, *Anti-cancer Drug Design*, 10, 103-118. Thus, prodrugs 5a-s were synthesized and evaluated.

Once the very practical synthesis of high purity prodrug 3d was in hand, a variety of cation derivatives of the parent phosphate were synthesized and evaluated. By treating the prodrug 3d phosphoric acid precursor with a 1.0 M solution of the respective metal hydroxide or acetate, the corresponding salts were formed. An analogous procedure was followed for the ammonium salts, using a 1.0 M solution of the amine in methanol. For the alkaloid salts, two equivalents of the base (presuming 100% formation of the phosphoric intermediate) in a suitable solvent were added to the acid solution and allowed to react for 6-8 hours. Precipitation or recrystallization gave the products.

3'-O-Bis(benzyl)phosphoryl-3,4,4',5-tetramethoxy-(E)-stilbene (4b)

(E)-combretastatin A-4 (4a, 2.2 g, 7 mmol) was dissolved in acetonitrile (20 ml) in a flask equipped with a septa, thermometer and argon inlet. After cooling to −25° C., carbon tetrachloride (3.38 ml, 35 mmol, 5 equiv) was added and the solution stirred for 5 minutes. With a syringe, diisopropylethylamine (2.56 ml, 14.7 mmol, 2.1 equiv) was added followed by DMAP (86 mg, 0.7 mmol, 0.1 equiv). Slow (dropwise) addition of dibenzyl phosphite (2.24 ml, 10.2 mmol, 1.45 equiv) was begun one minute later at such a rate that the reaction temperature remained below −20° C. The reaction was complete in 1 hour (by TLC analysis), 0.5 M $KH_2PO_4$ was added (5 ml), the solution allowed to warm to room temperature and extracted with ethyl acetate (3×20 ml). The combined solvent extract was washed with water (25 ml), saturated NaCl (25 ml) and dried. Filtration and removal of solvent gave an oil that was chromatographed on a column of silica gel (hexane-ethyl acetate, 3:2) to give phosphate ester 4b as a clear gum (3.96 g, 98%): $R_f$ 0.15 (hexane-ethyl acetate, 3:2); EIMS m/z (% intensity) 576 ($M^+$, 100), 561 (12), 486 (3), 406 (6), 394 (2), 378 (6), 364 (7), 316 (17), 301 (10), 252 (8), 241 (5), 181 (5); IR (neat) $v_{max}$ 3005, 2939, 2839, 1734, 1581, 1512, 1456, 1425, 1346, 1278, 1126, 1008, 900, 823, 740, 698 $cm^{-1}$; $^1$H-NMR (300 MHz) δ 3.80 (s, 3H, $OCH_3$), 3.87 (s, 3H, $OCH_3$), 3.91 (s, 6H, 2×$OCH_3$), 5.18 (s, 2H, $CH_2$—Ar), 5.21 (s, 2H, $CH_2$—Ar), 6.69 (s, 2H), 6.81 (d, J=16.5 Hz, 1H), 6.88 (d, J=16.5 Hz, 1H), 6.89 (d, J=9.3 Hz, 1H), 7.24 (m, 1H), 7.34 (s, 10H, Ar—H), 7.42 (t, J=3.3 Hz, 1H); $^{13}$C-NMR (75 MHz) δ 153.41, 150.22, 139.87, 135.78, 133.06, 130.57, 128.53, 127.93, 127.65, 126.82, 124.28, 119.00, 112.71, 103.47, 69.95, 60.97, 56.13; $^{31}$P-NMR (202 MHz) δ −5.52; Anal. calcd. for $C_{32}H_{33}O_8P$: C, 66.67; H, 5.77. Found: C, 66.71; H, 5.93.

Sodium (E)-combretastatin A-4 3'-O-phosphate (4c)

Chlorotrimethylsilane (0.88 ml, 6.9 mmol, 2 equiv) was slowly added (with vigorous stirring) to a solution of the benzyl ester (4b, 2.0 g, 3.5 mmol) and sodium iodide (1.04 g, 6.9 mmol, 2 equiv) in dry acetonitrile (10 ml, in a flame-dried flask under argon). After stirring for 20 minutes, TLC analysis (hexane-ethyl acetate, 3:2) showed no starting material. Enough water was added to dissolve the salts and the straw color removed by the addition of 10% aq. sodium thiosulfate (5 drops). The solvent was separated and the aqueous phase extracted with ethyl acetate (4×10 ml). The combined extract was concentrated in vacuo and the resulting foam was dissolved in dry methanol (100 ml). Sodium methoxide (95%, 375 mg, 6.9 mmol, 2 equiv) was added in one portion and the solution stirred for 6 hours. The methanol was removed under reduced pressure and the solid recrystallized from methanol-acetone to give an off-white powder (1.43 g, 93%): m.p. 157-158° C.; $R_f$ 0.45 (n-butanol-methanol-water-ammonia, 4:3:2:1); UV $\lambda_{max}$ 325 nm; IR (KBr) 2939, 2839, 1583, 1512, 1464, 1423, 1340, 1253, 1126, 991, 923, 856, 819, 773, 717, 644 $cm^{-1}$; $^1$H-NMR (500 MHz, $CD_3OD$) δ 3.73 (s, 3H, $OCH_3$), 3.84 (s, 3H, $OCH_3$), 3.87 (s, 6H, 2×$OCH_3$), 6.82 (s, 2H), 6.92 (d, J=8.5 Hz, 1H), 7.00 (d, J=16 Hz, 1H), 7.03 (d, J=16 Hz, 1H), 7.10 (dd, J=8.5 Hz, 2 Hz, 1H), 7.14 (d, J=2 Hz, 1H); $^{13}$C-NMR (75 MHz, $CD_3OD$) δ 153.12, 134.07, 130.47, 127.62, 126.35, 121.20, 117.66, 112.01, 103.16, 73.70, 59.69, 55.12; $^{31}$P-NMR (202 MHz, $CD_3OD$) δ −1.4; HRFABMS m/z 441.0698 $[M+Na]^+$, (calcd for $C_{18}H_{20}O_8Na_2P$, 441.0691).

General Procedure for Synthesis of Combretastatin A-4 Prodrugs

Method A (Prodrugs 5a-f)

Cesium combretastatin A-4 3'-O-phosphate (5b)

To a stirred solution of dibenzyl combretastatin A-4 3'-O-phosphate (4b, 0.50 g; 0.87 mmol) and sodium iodide (0.26 g, 1.74 mmol, 2 equiv) in dry acetonitrile (4 ml) in a flame-dried flask under argon was slowly added via syringe chlorotrimethylsilane (0.22 ml, 1.74 mmol, 2 equiv). The mixture was stirred at room temperature until the reaction was complete by TLC (ca 20 min). Enough water was added to dissolve the salts and the straw color was removed by the addition of 10% sodium thiosulfate (4 drops). The aqueous phase was extracted with ethyl acetate (4×5 ml) and the combined extract was concentrated under reduced pressure to a light straw foam. After adding distilled water (2 ml) and 1.0 M aqueous CsOH (1.74 ml, 1.74 mmol) dropwise, the solution became cloudy. The mixture was stirred for 6 hours under argon, whereupon the precipitate was collected and recrystallized from water-acetone to afford a colorless powder (0.51 g) m.p. 167-168° C.; $^1$H-NMR (300 MHz, $D_2O$) δ 3.70 (s, 6H, 2×$OCH_3$), 3.76 (s, 3H, $OCH_3$), 3.83 (s, 3H, $OCH_3$), 6.53 (d, J=12.3 Hz, 1H), 6.65 (d, J=12.3 Hz, 1H), 6.68 (s, 2H), 6.86 (d, J=8.4 Hz, 1H), 6.90 (dd, J=8.4, 1.8 Hz, 1H), 7.32 (d, J=1.8 Hz, 1H).

Calcium combretastatin A-4 3'-O-phosphate (5a)

Reprecipitated from water-acetone to give a colorless powder (147 mg): m.p. 293-295° C. (dec); $^1$H-NMR (300 MHz, $D_2O$) δ 3.69 (s, 6H, 2×$OCH_3$), 3.74 (s, 3H, $OCH_3$), 3.81 (s, 3H, OCH$_3$), 6.54 (d, J=12.4 Hz, 1H), 6.67 (d, J=12.4 Hz, 1H), 6.69 (s, 2H), 6.85 (d, J=8.1 Hz, 1H), 6.91 (dd, J=8.1, 1.8 Hz, 1H), 7.21 (d, J=1.8 Hz, 1H).

Lithium combretastatin A-4 3'-O-phosphate (5c)

Recrystallized from water-acetone to give a colorless powder (151 mg): m.p. 241-242° C.; $^1$H-NMR (300 MHz, D$_2$O) δ 3.56 (s, 6H, 2×OCH$_3$), 3.62 (s, 3H, OCH$_3$), 3.70 (s, 3H, OCH$_3$), 6.38 (d, J=12 Hz, 1H), 6.52 (s, 2H), 6.53 (d, J=12 Hz, 1H), 6.73 (dd, J=8.4, 1.4 Hz, 1H), 7.24 (bd, J=1.4 Hz, 1H).

Magnesium combretastatin A-4 3'-O-phosphate (5d)

Recrystallization from methanol-acetone afforded a creme-colored solid (121 mg): m.p. 270° C. (dec); $^1$H-NMR (300 MHz, D$_2$O) δ 3.54 (s, 6H, 2×OCH$_3$), 3.62 (s, 3H, OCH$_3$), 3.72 (s, 3H, OCH$_3$), 6.34 (d, J=12.3 Hz, 1H), 6.48 (s, 2H), 6.50 (d, J=12.3 Hz, 1H), 6.75 (m, 2H), 7.20 (s, 1H).

Manganese combretastatin A-4 3'-O-phosphate (5e)

Recrystallization from water-acetone gave a creme-colored solid (143 mg): m.p. 241-242° C. (dec); $^1$H-NMR (300 MHz, D$_2$O) δ 3.66 (s, 6H, 2×OCH$_3$), 3.73 (s, 3H, OCH$_3$), 3.82 (s, 3H, OCH$_3$), 6.46 (d, J=12.3 Hz, 1H), 6.58 (s, 2H), 6.59 (d, J=12.3 Hz, 1H), 6.87 (d, J=8.7 Hz, 1H), 6.94 (dd, J=8.7, 1.5 Hz, 1H), 7.24 (s, 1H).

Zinc combretastatin A-4 3'-O-phosphate (5f)

Collection of the white solid and washing with acetone gave a colorless, opalescent solid (164 mg): m.p. 198-200° C.; $^1$H-NMR (300 MHz, D$_2$O) δ 3.58 (s, 6H, 2×OCH;), 3.65 (s, 3H, OCH$_3$), 3.73 (s, 3H, OCH$_3$), 6.41 (d, J=12 Hz, 1H), 6.52 (s, 2H), 6.52 (d, J=12 Hz, 1H), 6.82 (d, J=8.1 Hz, 1H), 6.89 (dd, J=8.1, 1.4 Hz, 1H), 7.12 (d, J=1.4 Hz, 1H).

Method B (Prodrugs 5g-l)

The same general procedure as described above was used, except 2 equivalents of a 1.0 M solution of the amine in dry methanol was added and the reaction mixture allowed to stir for 8 h. All the amine salts were recrystallized from methanol-ether.

Imidazole combretastatin A-4 3'-O-phosphate (5 g)

Recrystallization gave 137 mg: m.p. 196-198° C.; $^1$H-NMR (300 MHz, D$_2$O) δ 3.66 (s, 6H, 2×OCH$_3$), 3.73 (s, 3H, OCH$_3$), 3.82 (s, 3H, OCH$_3$), 6.47 (d, J=12 Hz, 1H), 6.58 (s, 2H), 6.59 (d, J=12 Hz, 1H), 6.92 (dd, J=8.4, 1.2 Hz, 1H), 7.23 (d, J=1.2 Hz, 1H), 7.46 (s, 2H, 64, 65), 8.67 (s, 1H, 62).

Morpholine combretastatin A-4 3'-O-phosphate (5h)

Recrystallization afforded (121 mg 61% yield): m.p. 209-210° C.; $^1$H-NMR (300 MHz, D$_2$O) δ 3.22 (m, 4H, —CH$_2$OCH$_2$—), 3.46 (s, 6H, OCH$_3$), 3.48 (s, 3H, OCH$_3$), 3.54 (s, 3H, OCH$_3$), 3.88 (m, 4H, —CH$_2$NCH$_2$-), 6.36 (d, J=-12.3 Hz, 1H), 6.49 (s, 2H), 6.50 (d, J=12.3 Hz, 1H), 6.79 (dd, J=8.1, 1.2 Hz, 1H), 7.24 (bd, 8.1 Hz, 1H), 7.40 (bd, J=1.2 Hz, 1H).

Piperazine combretastatin A-4 3'-O-phosphate (5i)

Following recrystallization 151 mg: m.p. 198-200° C.; $^1$H-NMR (300 MHz, CD$_3$OD) δ 3.01 (bs, 1H, NH), 3.52 (bm, 8H, δ 2-H), 3.67 (s, 6H, 2×OCH$_3$), 3.74 (s, 3H, OCH$_3$), 3.83 (s, 3H, OCH$_3$), 6.49 (d, J=12 Hz, 1H), 6.56 (d, J=12 Hz, 1H), 6.62 (s, 2H), 6.95 (m, 2H), 7.24 (s, 1H).

Piperidine combretastatin A-4 3'-O-phosphate (5j)

By recrystallization 137 mg (was collected): m.p. =159-160° C.; $^1$H-NMR (300 MHz, D$_2$O) δ 1.67 (m, 8H, [2×δ 3 H s]), 1.77 (m, 4H, [2×δ 4H s]), 3.15 (m, 8H, [2×δ 2H s]), 3.66 (s, 6H, 2×OCH$_3$), 3.73 (s, 3H, OCH$_3$), 3.82 (s, 3H, OCH$_3$), 6.48 (d, J=12 Hz, 1H), 6.60 (s, 2H), 6.61 (d, J=12 Hz, 1H), 6.854 (d, J=8.5 Hz, 1H), 6.92 (dd, J=19.5, 8.5 Hz, 1H), 7.26 (s, 1H).

Pyrazole combretastatin A-4 3'-O-phosphate (5k)

Recrystallization produced 112 mg: m.p. =186-187° C.; $^1$H-NMR (300 MHz, D$_2$O) δ 3.69 (s, 6H, 2×OCH$_3$), 3.76 (s, 3H, OCH$_3$), 3.85 (s, 3H, OCH$_3$), 6.30 (d, J=1.4 Hz, 2H, 2×δ$_4$), 6.53 (d, J=12 Hz, 1H), 6.63 (d, J=12 Hz, 1H), 6.64 (s, 2H), 6.97 (m, 2H), 7.25 (d, J=1.8 Hz, 1H), 7.67 (d, 4H, 2×δ$_3$, δ$_5$H).

Pyridine combretastatin A-4 3'-O-phosphate (5l)

The yield was 96 mg: m.p. =165-168° C.; $^1$H-NMR (300 MHz, D$_2$O) δ 3.66 (s, 6H, 2_×OCH$_3$), 3.73 (s, 3H, OCH$_3$), 7.82 (s, 3H, OCH$_3$), 6.48 (d, J=12 Hz, 1H), 6.58 (s, 2H), 6.59 (d, J=12 Hz, 1H), 6.90 (d, J=8.4 Hz, 1H), 6.95 (dd, J=8.4, 1.5 Hz, 1H), 7.22 (bd, J=1.5 Hz, 1H), 7.47 (d, J=3.3 Hz, 4H, 2×δ$_{3,5}$—H), 8.0 (m, 2H, δ$_4$—H), 8.86 (m, 4H, 2×δ$_{2,6}$—H).

Method C (Prodrugs 5m-s)

An analogous method as summarized for prodrugs 3a-f was used, except that two equivalents of the alkaloid or other base in the appropriate solvent were added to the phosphoric acid in the same solvent. Recrystallization/precipitation was accomplished using methanol-ether.

Adenosine combretastatin A-4 3'-O-phosphate (5m)

The adenosine salt weighed 160 mg: m.p. 155-158° C.; $^1$H-NMR (300 MHz, D$_2$O) δ 3.50 (s, 6H, 2×OCH$_3$), 3.57 (s, 3H, OCH$_3$), 3.68 (s, 3H, OCH$_3$), 3.71 (d, J=2.1 Hx, 2H), 3.76 (bs, 2H), 3.80 (dd, J=2.1, 6.6 Hz, 1H), 4.14 (d, J=3.0 Hz, 2H), 4.28 (t, J=3.0 Hz, 2H), 4.58 (t, J=6.0 Hz, 2H), 5.85 (d, J=6.0 Hz, 2H), 6.21 (d, J=12.0 Hz, 1H), 6.32 (s, 2H), 6.36 (d, J=12.6 Hz, 1H), 6.71 (bs, 3H), 7.07 (s, 1H), 7.95 (d, J=1.5 Hz, 2H), 8.11 (s, 2H).

Cinchonine combretastatin A-4 3'-O-phosphate (5n)

The use of cinchonine led to 175 mg of product, m.p. 189-193° C.; $^1$H-NMR (300 MHz, CDCl$_3$) δ 0.829 (m, 1H), 1.21 (m, 1H), 1.74 (m, 1H), 2.15 (t, J=12 Hz, 1H), 2.32 (q, 1H), 3.30 (br s, —OH, 1H), 3.6 (s, 3H, OCH$_3$), 3.64 (s, 6H, 2×OCH$_3$), 3.78 (s, 3H, OCH$_3$), 4.45 (t, J=9.3 Hz, 1H), 5.18 (d, J=16 Hz, 1H), 5.23 (d, J=10.8 Hz, 1H), 5.42 (d, J=12 Hz, 1H), 5.87 (m, 1H), 7.7 (d, J=8.4 Hz, 1H), 7.76 (d, J=6.3 Hz, 1H), 7.86 (d, J=4.5 Hz, 1H), 7.97 (d, J=8.7 Hz, 1H), 8.10 (d, J=8.7 Hz, 1H), 8.29 (d, J=8.4 Hz, 1H), 8.83 (d, J=4.5 Hz, 1H):

Glucosamine combretastatin A-4 3'-O-phosphate (5o)

Recrystallization led to 98 mg of product, m.p. 190-195° C. (dec); $^1$H-NMR (300 MHz, CD$_3$OD) δ 1.81 (s), 1.88 (s), 1.93 (s), 2.85 (s), 2.88 (d, J=2.1 Hz, 1H), 2.91 (s, 1H), 3.16 (d, J=3.9 Hz, 1H), 3.19 (d, J=3.9 Hz, 1H), 3.38 (h, 2H), 3.53-3.82 (m, 4H), 3.64 (s, 3H, OCH$_3$), 3.69 (s, 3H, OCH$_3$), 3.74 (s, 6H, 2×OCH$_3$), 4.82 (d, J=8.1 Hz, 1H), 5.33 (d, J=3.3 Hz, 1H), 6.51 (d, J=12.1 Hz, 1H), 6.60 (d, J=12.1 Hz, 1H), 6.63 (s, 2H), 6.80-7.22 (m, 3H).

Quinine combretastatin A-4 3'-O-phosphate (5p)

Recrystallization of the quinine salt gave 75 mg: m.p. 179-184° C.; $^1$H-NMR (300 MHz, CD$_3$OD) δ 3.00 (q, 10.1, 13.7 Hz, 1H), 3.15 (o, J=5.0, 8.9, 8.9 Hz, 1H), 3.37 (h, J=3.0, 5.3, 10.1, 13.2 Hz, 1H), 3.41 (bs, 1H, OH), 3.61 (s, 3H, OCH$_3$), 3.69 (s, 3H, OCH$_3$), 3.82 (s, 6H, 2×OCH$_3$), 3.91 (s, 3H, OCH$_3$),4.90 (d, J=10.0 Hz, 1H), 4.97 (d, J=17.1 Hz, 1H), 5.50 (d, J=4.4 Hz, 1H), 5.84 (o, J=7.6, 10.0, 17.3 Hz, 1H), 6.55 (bd, J=12.6 Hz, 1H), 6.61 (bd, J=12.6 Hz, 1H), 6.63 (s, 2H), 6.67 (bs, 3H), 7.22 (s, 1H), 7.34 (d, J=9.5 Hz, 1H), 7.50 (d, J=4.3 Hz, 1H), 8.70 (d, J=4.2 Hz, 1H).

Quinidine combretastatin A-4 3'-O-phosphate (5q)

Quinidine was used to prepare 300 mg of product, m.p. 180-181° C.; $^1$H-NMR (300 MHz, CD$_3$OD) δ 0.963 (t, 1H), 1.16 (m, 1H), 1.89 (m, 2H), 1.99 (bs, 1H), 2.34 (t, J=6.8 Hz, 1H), 2.65 (dd, J=6.6 Hz, 12.3 Hz, 1H), 3.10 (s, 1H), 3.22 (m, 1H), 3.29 (o, J=1.6, 7.9, 14 Hz), 3.32 (s, 3H, OCH$_3$), 3.65 (s, 3H, OCH$_3$), 3.99 (s, 3H, OCH$_3$), 4.09 (s, 6H, 2×OCH$_3$), 4.61 (bs, 1H), 5.10 (d, J=9.3 Hz), 5.28 (d, J=15.4 Hz, 1H), 5.96 (bs, 1H), 6.11 (o, J=7.4, 10.5, 16.0 Hz, 1H), 6.54 (bd, J=12.0 Hz, 1H), 6.60 (bd, J=12 Hz, 1H), 6.61 (s, 2H), 7.43 (dd, J=6.9, 1.8 Hz, 1H), 7.56 (dd, J=7.2, 1.8 Hz, 1H), 7.61 (d, J=1.8 Hz), 7.70 (t, J=3.3 Hz, 1H), 7.91 (d, J=4.4 Hz, 1H), 7.97 (d, J=9.2 Hz, 1H), 8.06 (d, J=9.2 Hz, 1H), 8.69 (d, J=4.4 Hz, 1H), 8.79 (d, J=4.8 Hz, 1H).

Tetracycline combretastatin A-4 3'-O-phosphate (5r)

The tetracycline salt upon recrystallization weighed 136 mg: m.p. 191-193° C.; $^1$H-NMR (300 MHz, DMSO-d$_6$) δ 1.53-3.21 (m, 4H, C$_4$α and C$_5$α methine protons, C$_5$-methylene hydrogens), 1.56 (s, 3H, C$_6$—CH$_3$), 2.55 (s, 6H, N(CH$_3$)$_2$), 3.31 (bs, 1H, C$_4$—H), 3.64 (s, 6H, 2×OCH$_3$), 3.67 (s, 3H, OCH$_3$), 3.72 (s, 3H, OCH$_3$), 4.31 (bs, 1H, C$_4$—H), 6.41 (d, J=12.6, 1H), 6.49 (d, J=12.6, 1H), 6.61 (s, 2H), 6.87 (s, 3H), 6.93 (d, J=8.1, 1H, D—Ar—H), 7.14 (d, J=7.8, 1H, D—Ar—H), 7.47 (s, 1H), 7.56 (t, J=7.8, 1H, D—Ar—H), 9.13 (bs, 2H, CONH$_2$), 11.7 (bs, 1H, C$_{10}$—OH).

Verapamil combretastatin A-4 3'-O-phosphate (5s)

From verapamil was obtained 110 mg of product: m.p. 185-186° C.; $^1$H-NMR (300 MHz, CD$_3$OD) δ 0.73 (d, J=6.6 Hz, 3H), 1.15 (d on m, J=6.6 Hz, 4H), 1.32 (m, 1H), 1.65 (m, 1H), 1.99 (s, 1H), 2.17 (m, 1H), 2.19 (s, 1H), 2.78 (bs, 2H), 3.11 (m, 2H), 3.27 (bs, 2H), 3.36-3.82 (4s, 8×OCH$_3$, 24H), 6.47 (d, J=12 Hz, 1H), 6.57 (d, J=12 Hz, 1H), 6.64 (bd, 11H), 6.80 (bd, 1H), 6.92 (dd, J=8.4, 1.9 Hz, 2H), 7.28 (s, 1H).

Biological Results

All of the synthetic products were evaluated against a minipanel of human cancer cell lines, the murine P388 lymphocytic leukemia and a selection of microorganisms. These results are summarized in Tables I-III respectively.

In the case of Antimicrobial susceptibility testing compounds were screened against the bacteria *Stenotrophomonas maltophilia*, *Micrococcus luteus*, *Staphylococcus aureus*, *Escherichia coli*, *Enterobacter cloacae*, *Enterococcus faecalis*, *Streptococcus pneumoniae*, *Neisseria gonorrhoeae*, and the fungi *Candida albicans* and *Cryptococcus neoformans*, according to established disk susceptibility testing protocols (National Committee for Clinical Laboratory Standards, 1997).

TABLE I

Human Cancer Cell Line Activity (GI$_{50}$ (μg/ml)) and Murine P-388 Leukemia Inhibitory Activity (ED$_{50}$ (μg/ml)) of combretastatin A-4 (1a) and synthetic modifications (4a-5s).

| Structure | Prostate DU-145 | Pharynx FADU | Lung-NSC NCI-H460 | Thyroid SW1736 |
|---|---|---|---|---|
| 1a | 0.00076 | 0.00065 | 0.00056 | 0.00071 |
| 3d | 0.0072 | 0.0045 | 0.0035 | 0.0061 |
| 4a | 0.037 | 0.040 | 0.038 | 0.080 |
| 4c | 0.044 | 0.071 | 0.038 | 11.2 |
| 5a | 0.001 | 0.001 | 0.001 | 0.010 |
| 5b | 0.0028 | 0.0023 | 0.0032 | 8.4 |
| 5c | 0.0025 | 0.003 | 0.004 | 0.030 |
| 5d | 0.01 | 0.031 | 0.017 | 6.8 |
| 5e | <0.001 | 0.00091 | 0.0015 | 14.7 |
| 5f | 0.0062 | 0.0070 | 0.0074 | 0.059 |
| 5g | 0.001 | 0.01 | 0.004 | 0.011 |
| 5h | 0.0024 | 0.0016 | 0.003 | 0.02 |
| 5i | 0.0011 | 0.0018 | 0.0028 | 23.5 |
| 5j | 0.01 | 0.01 | 0.01 | 0.50 |
| 5k | 0.01 | 0.01 | 0.01 | 4.6 |
| 5l | 0.036 | 0.032 | 0.038 | 0.01 |
| 5m | 0.036 | 0.032 | 0.038 | 0.092 |
| 5n | 0.030 | 0.024 | 0.037 | 0.089 |
| 5o | 0.026 | 0.015 | 0.034 | 0.061 |
| 5p | 0.0048 | 0.006 | 0.0042 | 7.5 |
| 5q | 0.0036 | 0.0033 | 0.0039 | 0.11 |
| 5r | 0.058 | 0.0055 | 0.0046 | 0.012 |
| 5s | 0.0036 | 0.0046 | 0.004 | 0.0061 |

| Structure | Neuroblast SK-N-SH | Pancreas BXPC-3 | Melanoma SK-Mel-3 | P-388 |
|---|---|---|---|---|
| 1a | 0.00026 | >0.1 | 0.00020 | 0.00266 |
| 3d | 0.0025 | 0.23 | NT[a] | 0.00292 |
| 4a | 0.029 | 3.9 | NT[a] | 0.280 |
| 4c | 3.1 | 4.0 | 0.036 | 0.02 |
| 5a | 0.015 | 0.22 | 0.0036 | 0.0011 |
| 5b | 0.011 | 0.31 | 0.0043 | 0.001 |
| 5c | 0.016 | 0.31 | NT[a] | 0.0012 |
| 5d | 0.01 | 0.43 | NT[a] | 0.0018 |
| 5e | 0.014 | 0.20 | 0.0036 | 0.016 |
| 5f | 0.024 | 1.1 | 1.0 | 0.0343 |
| 5g | 0.01 | 0.39 | 0.01 | 0.0025 |
| 5h | 0.039 | 0.26 | 0.0042 | 0.0023 |
| 5i | 0.021 | 0.19 | 0.0036 | 0.0016 |
| 5j | 0.017 | 0.30 | 0.01 | 0.0029 |
| 5k | 0.014 | 0.23 | 0.01 | 0.0023 |
| 5l | 0.03 | 11.6 | 0.35 | <0.001 |
| 5m | 0.034 | 11.6 | 0.35 | 0.16 |
| 5n | NT[a] | 1.6 | NT[a] | 0.020 |
| 5o | 0.016 | 4.5 | NT[a] | 0.0164 |
| 5p | NT[a] | 2.2 | NT[a] | 0.027 |
| 5q | NT[a] | 0.43 | NT[a] | 0.0032 |
| 5r | 0.0032 | 0.57 | NT[a] | 0.037 |
| 5s | 0.0025 | 0.46 | NT[a] | 0.001 |

[a]Not tested against this cell line

TABLE II

Antimicrobial activity of combretastatin A-4 (1a), combretastatin A-4 Prodrug (3d) and synthetic modifications (4a, 4c, 5a-s).

| Compound | Microbe(s) inhibited | Minimum inhibitory concentration (μg/disk) |
|---|---|---|
| 1a | *Neisseria gonorrhoeae* | 25-50 |
| 3d | *Neisseria gonorrhoeae* | 50-100 |
| 4a | *Micrococcus luteus* | 25-50 |
| 4c | *Neisseria gonorrhoeae* | 50-100 |
| 5a | * | |
| 5b | * | |
| 5c | * | |

TABLE II-continued

Antimicrobial activity of combretastatin A-4 (1a), combretastatin A-4 Prodrug (3d) and synthetic modifications (4a, 4c, 5a-s).

| Compound | Microbe(s) inhibited | Minimum inhibitory concentration (μg/disk) |
|---|---|---|
| 5d | * | |
| 5e | Neisseria gonorrhoeae | 6.25-12.5 |
| | Candida albicans | 25-50 |
| | Cryptococcus neoformans | 12.5-25 |
| 5f | * | |
| 5g | * | |
| 5h | * | |
| 5i | Neisseria gonorrhoeae | 25-50 |
| | Candida albicans | 50-100 |
| | Cryptococcus neoformans | 25-50 |
| 5j | * | |
| 5k | * | |
| 5l | * | |
| 5m | * | |
| 5n | Neisseria gonorrhoeae | 25-50 |
| 5o | * | |
| 5p | * | |
| 5q | Neisseria gonorrhoeae | 6.25-12.5 |
| 5r | Neisseria gonorrhoeae | 3.12-6.25 |
| | Escherichia coli | 3.12-6.25 |
| | Stenotrophomonas maltophilia | 6.25-12.5 |
| | Enterobacter cloacae | 3.12-6.25 |
| | Micrococcus luteus | 0.78-1.56 |
| | Streptococcus pneumoniae | 0.195-0.39 |
| | Staphylococcus aureus | 0.195-0.39 |
| | Enterococcus faecalis | 25-50 |
| 5s | * | |

* At 100 μg/disk no inhibition of the eight bacteria and two fungi tested.

TABLE III

Solubility of combretastatin A-4 prodrug 3d, (E)-stilbene prodrug 4c and structural modifications 5a–s in mg per 1 ml water at 25° C.

| Compound | 3d | 4c | 5a | 5b | 5c | 5d | 5e | 5f | 5g | 5h |
|---|---|---|---|---|---|---|---|---|---|---|
| Solubility (mg/ml) | 20 | 4 | 2 | >50 | 6 | 7 | 3 | 11 | 10 | 9 |

| Compound | 5i | 5j | 5k | 5l | 5m | 5n | 5o | 5p | 5q | 5r | 5s |
|---|---|---|---|---|---|---|---|---|---|---|---|
| Solubility (mg/ml) | 1 | 5 | 8 | 3 | 4 | 4 | 15 | 6 | 2 | 1 | 16 |

Combretastatin A-4, combretastatin A-4 prodrug and several prodrug modifications inhibited growth of the pathogenic bacterium *Neisseria gonorrhoeae* (Table II). Addition of manganese 5e and piperazine 5i to the parent phosphate yielded compounds inhibitor, to opportunistic fungi. As expected, the tetracycline derivative 5r inhibited the growth of all Gram-negative and Gram-positive bacteria tested.

Biological Evaluation and Statistical Definitions

The following measures are used to express drug activity by giving the drug dose which reduces cell growth to a specified percentage of growth: $ED_{50}$ (P388) and $GI_{50}$, (HTCL) are the drug doses (in μg/ml of cancer cells) needed to reduce the cancer cells by 50%. There is no mathematical difference between $ED_{50}$ and $GI_{50}$, which are both calculated using the same formula. The only difference is historical usage.

Total Growth Inhibition ("TGI") is the drug dose (in μg/ml of cancer cells) needed to yield zero percent growth. Whether just as many cells were killed as were produced (steady state), or no growth occurred (total inhibition), cannot be distinguished.

Lethal Concentration 50% ("$LC_{50}$") is the drug concentration (in μg/ml of cancer cells) kills half of the cells originally present at the beginning of the experiment.

Each drug is tested at five (5) doses: 100-10-1-0.1-0.01 μg/ml. Percent Growths are calculated for each dose. The two (or three) doses with growth values above, below, (or near to) 50% growth are used to calculate the $ED_{50}/GI_{50}$ using a linear regression formula. The log of the dose is used during the regression computation. If no dose yields a growth value under 50%, the results are expressed as: $ED_{50}$>(highest dose). If no dose yields growth higher than 50% growth, then $ED_{50}$<(lowest dose). Similar calculations are performed for the TGI at 0% growth, and at -50% growth for the $LC_{50}$.

Percent of Growth

At the start of an experiment, cells from the in vitro cell cultures are inoculated into the appropriate tubes or microtiter plates. One set of control tubes/plates is immediately counted to determine the number of cells at the start of the experiment. This is the "baseline count", or "$T_{zero}$ reading". At the end of the experiment (48 hours later) a second set of Control tubes/plates is analyzed to determine the "Control Growth" value. The growth (or death) of cells relative to the initial quantity of cells is used to define the "Percent of Growth".

EXAMPLE

Baseline Count = 20

Control Count = 200

(10-Fold Growth)

| | |
|---|---|
| 100% Growth = Control Growth | 1 |
| 50% Growth = $T_{zero}$ + $\underline{Control\text{-}T_{zero}}$ | 50% Growth = 110 |
| 0% Growth = $T_{zero}$ | 0% Growth = 20 |
| -50% Growth = $T_{zero}/2$ | -50% Growth = 10 |

For further information about the testing protocols and procedures see Anne Monks et al., "Feasibility of a High-Flux Anticancer Drug Screen Using a Diverse Panel of Cultured Human Tumor Cell Lines", 83 *J. Nat. Cancer Inst.*, No. 11, pp. 757-66 (5 Jun. 1991) and Michael J. Boyd, "Status of the NCI Preclinical Antitumor Drug Discovery Screen", 3 *Princ. & Practice of Oncology Updates*, No. 10, pp. 1-12 (October 1989).

By definition a "prodrug" is a precursor which will undergo metabolic activation in vivo to the active drug. Thus, certain phosphate derivatives make ideal prodrugs if the phosphate group can be cleaved by endogenous non-specific phosphatases (McComb et al., *Alkaline Phosphatase*, New York: Plenum Press, 1979) As previously reported (See, U.S. Pat. Nos. 4,996,237 and 5,561,122), a preliminary in vitro comparison of the stable combretastatin A-4 phosphate metal or ammonium salts against the P388 murine leukemia and a selection of six human tumor cell lines (OVCAR-3, SF-295, A498, NCI-H460, KM20L2, SK-MEL-5) was performed using the sulforhodamine B assay (Skehan et al., "New Colorimetric Cytotoxiciry Assay for Anticancer-Drug Screening," *J. Nat. Cancer Inst.*, 1107 (1990)). Again, sodium phosphate derivative 3d is an equivalent to the derivative 1h disclosed earlier. The assay results relative to 1h will thus be repeated here with respect to 3d. Combretastatin A-4 1a and prodrug 1h (3d) were then comparatively evaluated against the full-panel NCI screen (Boyd, "Status of the NCI Preclinical Antitumor Drug Discovery Screen: Implications for Selection of New Agents for Clinical trial," 3 *Cancer: Principles and Practice of Oncology Updates*, No. 10, pp. 1-12 (1989); and Boyd et al., "The Future of New Drug Development, Section I, Introduction to Cancer Therapy," *Current Therapy in Oncology*, Philadelphia: Decker (1993)). Both were tested in quadruplicate at each of three different concentration ranges ($10^{-5}$, $10^{-6}$ and $10^{-7}$M upper limits, five, $\log_{10}$-spaced concentrations in each range). Optimal tests were selected for overall potency and differential cytotoxicity comparisons (Boyd and Paul, "Some Practical Considerations and Applications of the NCI in vitro Anticancer Drug Discovery Screen," *Drug Development Research*, (In Press)). The mean panel $GI_{50}$ concentration for the parent compound 1a was $6.61\pm0.79\times 10^{-9}$M, compared to $6.89\pm0.96\times10^{-9}$M for prodrug 1h (3d). TGI-COMPARE analyses (Id.) revealed a very high Pearson correlation coefficient of 0.91 for the differential cytotoxicity profiles of combretastatin A-4 1a and its prodrug 1h (3d). This high correlation coefficient reflects similarities in biological properties and/or chemical structure and properties. Paull et al., "Display and analysis of Patterns of Differential Activity of Drugs Against Human Tumor Cell Lines: Development of Mean Graph and COMPARE Algorithm," 81 *J. Nat. Cancer Inst.*, No. 14, pp. 108-92 (Jul. 19, 1989).

Clearly, the excellent water solubility of sodium phosphate 1h (3d), good stability and cell growth inhibitory activity comparable to combretastatin 1a allowed selection of this prodrug candidate for drug formulation studies. In a like manner, it is believed that any of the combretastatin A-4 phosphate metal or ammonium salts can be synthesized and utilized as prodrugs with cell growth inhibitory activity comparable to combretastatin 1a.

Based upon the foregoing, compositions 1h (3d) are believed useful in the treatment of one or more neoplastic diseases. For example, acute myelocytic leukemia, acute lymphocytic leukemia, malignant melanoma, adenocarcinoma of lung, neuroblastoma, small cell carcinoma of the lung, breast carcinoma, colon carcinoma, ovarian carcinoma, bladder carcinoma, and the like.

The dosage administered will be dependent upon the identity of the neoplastic disease; the type of host involved, including its age, health and weight; the kind of concurrent treatment, if any; the frequency of treatment and therapeutic ratio.

Illustratively, dosage levels of the administered active ingredients are: intravenous, 0.1 to about 20 mg/kg; intramuscular, 1 to about 50 mg/kg; orally, 5 to about 100 mg/kg; intranasal instillation, 5 to about 100 mg/kg; and aerosol, 5 to about 100 mg/kg of host body weight.

Expressed in terms of concentration, an active ingredient can be present in the compositions of the present invention for localized use about the cutis, intranasally, pharyngolaryngeally, bronchially, intravaginally, rectally, or ocularly in a concentration of from about 0.01 to about 50% w/w of the composition; preferably about 1 to about 20% w/w of the composition; and for parenteral use in a concentration of from about 0.05 to about 50% w/v of the composition and preferably from about 5 to about 20% w/v.

The compositions of the present invention are preferably presented for administration to humans and animals in unit dosage forms, such as tablets, capsules, pills, powders, granules, suppositories, sterile parenteral solutions or suspensions, sterile non-parenteral solutions of suspensions, and oral solutions or suspensions and the like, containing suitable quantities of an active ingredient.

For oral administration either solid or fluid unit dosage forms can be prepared.

Powders are prepared quite simply by comminuting the active ingredient to a suitably fine size and mixing with a similarly comminuted diluent. The diluent can be an edible carbohydrate material such as lactose or starch. Advantageously, a sweetening agent or sugar is present as well as a flavoring oil.

Capsules are produced by preparing a powder mixture as hereinbefore described and filling into formed gelatin sheaths. Advantageously, as an adjuvant to the filling operation, a lubricant such as talc, magnesium stearate, calcium stearate and the like is added to the powder mixture before the filling operation.

Soft gelatin capsules are prepared by machine encapsulation of a slurry of active ingredients with an acceptable vegetable oil, light liquid petrolatum or other inert oil or triglyceride.

Tablets are made by preparing a powder mixture, granulating or slugging, adding a lubricant and pressing into tablets. The powder mixture is prepared by mixing an active ingredient, suitably comminuted, with a diluent or base such as starch, lactose, kaolin, dicalcium phosphate and the like. The powder mixture can be granulated by wetting with a binder such as corn syrup, gelatin solution, methylcellulose solution or acacia mucilage and forcing through a screen. As an alternative to granulating, the powder mixture can be slugged, i.e., run through the tablet machine and the resulting imperfectly formed tablets broken into pieces (slugs). The slugs can be lubricated to prevent sticking to the tablet-forming dies by means of the addition of stearic acid, a stearic salt, talc or mineral oil. The lubricated mixture is then compressed into tablets.

Advantageously, the tablet can be provided with a protective coating consisting of a sealing coat or enteric coat of shellac, a coating of sugar and methylcellulose and polish coating of carnauba wax.

Fluid unit dosage forms for oral administration such as in syrups, elixirs and suspensions can be prepared wherein each teaspoonful of composition contains a predetermined amount of an active ingredient for administration. The water-soluble forms can be dissolved in an aqueous vehicle together with sugar, flavoring agents and preservatives to form a syrup. An elixir is prepared by using a hydroalcoholic vehicle with suitable sweeteners together with a flavoring agent. Suspensions can be prepared of the insoluble forms with a suitable vehicle with the aid of a suspending agent such as acacia, tragacanth, methylcellulose and the like.

For parenteral administration, fluid unit dosage forms are prepared utilizing an active ingredient and a sterile vehicle, water being preferred. The active ingredient, depending on the form and concentration used, can be either suspended or dissolved in the vehicle. In preparing solutions the water-soluble active ingredient can be dissolved in water for injection and filter sterilized before filling into a suitable vial or ampule and sealing. Advantageously, adjuvants such as a local anesthetic, preservative and buffering agents can be dissolved in the vehicle. Parenteral suspensions are prepared in substantially the same manner except that an active ingredient is suspended in the vehicle instead of being dissolved and sterilization cannot be accomplished by filtration. The active ingredient can be sterilized by exposure to ethylene oxide before suspending in the sterile vehicle.

Advantageously, a surfactant or wetting agent is included in the composition to facilitate uniform distribution of the active ingredient.

In addition to oral and parenteral administration, the rectal and vaginal routes can be utilized. An active ingredient can be administered by means of a suppository. A vehicle which has a melting point at about body temperature or one that is readily soluble can be utilized. For example, cocoa butter and various polyethylene glycols (Carbowaxes) can serve as the vehicle.

For intranasal-instillation, a fluid unit dosage form is prepared utilizing an active ingredient and a suitable pharmaceutical vehicle, preferably P.F. water, a dry powder can be formulated when insufflation is the administration of choice.

For use as aerosols, the active ingredients can be packaged in a pressurized aerosol container together with a gaseous or liquified propellant, for example, dichlorodifluoromethane, carbon dioxide, nitrogen, propane, and the like, with the usual adjuvants such as cosolvents and wetting agents, as may be necessary or desirable.

The term "unit dosage form" as used in the specification and claims refers to physically discrete units suitable as unitary dosages for human and animal subjects, each unit containing a predetermined quantity of active material calculated to produce the desired therapeutic effect in association with the required pharmaceutical diluent, carrier or vehicle. The specifications for the novel unit dosage forms of this invention are dictated by and are directly dependent on (a) the unique characteristics of the active material and the particular therapeutic effect to be achieved, and (b) the limitation inherent in the art of compounding such an active material for therapeutic use in humans, as disclosed in this specification, these being features of the present invention. Examples of suitable unit dosage forms in accord with this invention are tablets, capsules, troches, suppositories, powder packets, wafers, cachets, teaspoonfuls, tablespoonfuls, dropperfuls, ampules, vials, segregated multiples of any of the foregoing, and other forms as herein described.

The active ingredients to be employed as antineoplastic agents can be easily prepared in such unit dosage form with the employment of pharmaceutical materials which themselves are available in the art and can be prepared by established procedures. The following preparations are illustrative of the preparation of the unit dosage forms of the present invention, and not as a limitation thereof. Several dosage forms were prepared embodying the present invention. They are shown in the following examples in which the notation "active ingredient" signifies either of the combretastatin A-4 phosphate metal or ammonium salts, e.g. 3d, or structural modifications 4a, 4c and/or 5a-s.

Composition "A"

Hard-Gelatin Capsules

One thousand two-piece hard gelatin capsules for oral use, each capsule containing 200 mg of an active ingredient are prepared from the following types and amounts of ingredients:

| | |
|---|---|
| Active ingredient, micronized | 200 g |
| Corn Starch | 20 g |

-continued

| | |
|---|---|
| Talc | 20 g |
| Magnesium stearate | 2 g |

The active ingredient, finely divided by means of an air micronizer, is added to the other finely powdered ingredients, mixed thoroughly and then encapsulated in the usual manner.

The foregoing capsules are useful for treating a neoplastic disease by the oral administration of one or two capsules one to four times a day.

Using the procedure above, capsules are similarly prepared containing an active ingredient in 50, 250 and 500 mg amounts by substituting 50 g, 250 g and 500 g of an active ingredient for the 200 g used above.

Composition "B"

Soft Gelatin Capsules

One-piece soft gelatin capsules for oral use, each containing 200 mg of an active ingredient, finely divided by means of an air micronizer., are prepared by first suspending the compound in 0.5 ml of corn oil to render the material capsulatable and then encapsulating in the above manner.

The foregoing capsules are useful for treating a neoplastic disease by the oral administration of one or two capsules one to four times a day.

Composition "C"

Tablets

One thousand tablets, each containing 200 mg of an active ingredient, are prepared from the following types and amounts of ingredients:

| | |
|---|---|
| Active ingredient, micronized | 200 g |
| Lactose | 300 g |
| Corn starch | 50 g |
| Magnesium stearate | 4 g |
| Light liquid petrolatum | 5 g |

The active ingredient, finely divided by means of an air micronizer, is added to the other ingredients and then thoroughly mixed and slugged. The slugs are broken down by forcing them through a Number Sixteen screen. The resulting granules are then compressed into tablets, each tablet containing 200 mg of the active ingredient.

The foregoing tablets are useful for treating a neoplastic disease by the oral administration of one or two tablets one to four times a day.

Using the procedure above, tablets are similarly prepared containing an active ingredient in 250 mg and 100 mg amounts by substituting 250 g and 100 g of an active ingredient for the 200 g used above.

Composition "D"

Oral Suspension

One liter of an aqueous suspension for oral use, containing in each teaspoonful (5 ml) dose, 50 mg of an active ingredient, is prepared from the following types and amounts of ingredients:

| | |
|---|---|
| Active ingredient, micronized | 10 g |
| Citric acid | 2 g |
| Benzoic acid | 1 g |
| Sucrose | 790 g |
| Tragacanth | 5 g |
| Lemon Oil | 2 g |
| Deionized water, q.s. 1000 ml | |

The citric acid, benzoic acid, sucrose, tragacanth and lemon oil are dispersed in sufficient water to make 850 ml of suspension. The active ingredient, finely divided by means of an air micronizer, is stirred into the syrup unit uniformly distributed. Sufficient water is added to make 1000 ml.

The composition so prepared is useful for treating a neoplastic disease at a dose of 1 teaspoonful (15 ml) three times a day.

Composition "E"

Parenteral Product

A sterile aqueous suspension for parenteral injection, containing 30 mg of an active ingredient in each milliliter for treating a neoplastic disease, is prepared from the following types and amounts of ingredients:

| | |
|---|---|
| Active ingredient, micronized | 30 g |
| POLYSORBATE 80 | 5 g |
| Methylparaben | 2.5 g |
| Propylparaben | 0.17 g |
| Water for injection, q.s. 1000 ml. | |

All the ingredients, except the active ingredient, are dissolved in the water and the solution sterilized by filtration. To the sterile solution is added the sterilized active ingredient, finely divided by means of an air micronizer, and the final suspension is filled into sterile vials and the vials sealed.

The composition so prepared is useful for treating a neoplastic disease at a dose of 1 milliliter (1 ml) three times a day.

Composition "F"

Suppository, Rectal and Vaginal

One thousand suppositories, each weighing 2.5 g and containing 200 mg of an active ingredient are prepared from the following types and amounts of ingredients:

| | |
|---|---|
| Active ingredient, micronized | 15 g |
| Propylene glycol | 150 g |
| Polyethylene glycol #4000, q.s. | 2,500 g |

The active ingredient is finely divided by means of an air micronizer and added to the propylene glycol and the mixture passed through a colloid mill until uniformly dispersed. The polyethylene glycol is melted and the propylene glycol dispersion is added slowly with stirring. The suspension is poured into unchilled molds at 40° C. The composition is allowed to cool and solidify and then removed from the mold and each suppository foil wrapped.

The foregoing suppositories are inserted rectally or vaginally for treating a neoplastic disease.

Composition "G"

Intranasal Suspension

One liter of a sterile aqueous suspension for intranasal instillation, containing 20 mg of an active ingredient in each milliliter, is prepared from the following types and amounts of ingredients:

| | |
|---|---|
| Active ingredient, micronized | 15 g |
| POLYSORBATE 80 | 5 g |
| Methylparaben | 2.5 g |
| Propylparaben | 0.17 g |
| Deionized water, q.s. 1000 ml. | |

All the ingredients, except the active ingredient, are dissolved in the water and the solution sterilized by filtration. To the sterile solution is added the sterilized active ingredient, finely divided by means of an air micronizer, and the final suspension is aseptically filled into sterile containers.

The composition so prepared is useful for treating a neoplastic disease, by intranasal instillation of 0.2 to 0.5 ml given one to four times per day.

An active ingredient can also be present in the undiluted pure form for use locally about the cutis, intranasally, pharyngolaryngeally, bronchially, or orally.

Composition "H"

Powder

Five grams of an active ingredient in bulk form is finely divided by means of an air micronizer. The micronized powder is placed in a shaker-type container.

The foregoing composition is useful for treating a neoplastic disease, at localized sites by applying a powder one to four times per day.

Composition "I"

Oral Powder

One hundred grams of an active ingredient in bulk form is finely divided by means of an air micronizer. The micronized powder is divided into individual doses of 200 mg and packaged.

The foregoing powders are useful for treating a neoplastic disease, by the oral administration of one or two powders suspended in a glass of water, one to four times per day.

Composition "J"

Insufflation

One hundred grams of an active ingredient in bulk form is finely divided by means of an air micronizer.

The foregoing composition is useful for treating a neoplastic disease, by the inhalation of 300 mg one to four times a day.

The invention claimed is:

1. A compound of Formula I:

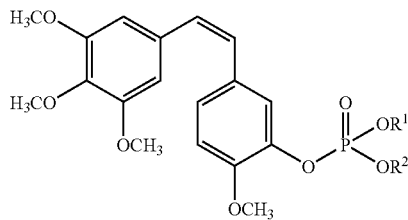

(I)

wherein:
one of —OR$_1$ or —OR$_2$ is O$^-$Na$^+$, and the other is hydroxyl.

2. A composition comprising the compound of claim 1.

3. The composition of claim 2, further comprising a compound of Formula I:

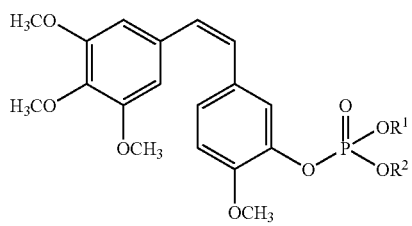

(I)

wherein:
—OR$_1$ and —OR$_2$ are both O$^-$Na$^+$.

4. A pharmaceutical composition comprising the compound of claim 1 and a pharmaceutically acceptable carrier thereof.

5. A pharmaceutical unit dosage form comprising the compound of claim 1.

6. The dosage form of claim 5, wherein the dosage form is selected from the group consisting of a tablet, a capsule, an oral suspension, an intranasal suspension, an insufflation, a troche, a suppository, a powder packet, a wafer, a cachet, an ampule, and a vial.

7. The dosage form of claim 5, which is a topical dosage form.

8. A method of modulating tumor growth or metastasis in an animal suffering from a neoplastic disease comprising administering to the animal an effective amount of a compound having a general structure of Formula I:

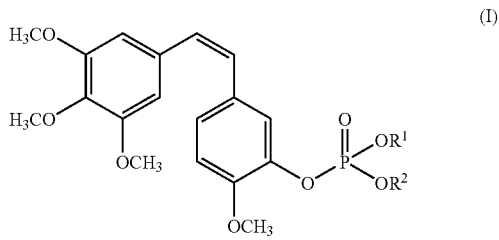

(I)

wherein:
one of —OR$_1$ or —OR$_2$ is O$^-$Na$^+$, and the other is hydroxyl.

9. The method of claim 8, wherein the neoplastic disease is selected from the group consisting of acute myelocytic leukemia, acute lymphocytic leukemia, malignant melanoma, adenocarcinoma of the lung, neuroblastoma, small cell carcinoma of the lung, breast carcinoma, colon carcinoma, ovarian carcinoma, and bladder carcinoma.

10. The method of claim 8, wherein the compound is administered intravenously.

11. The method of claim 10, wherein the effective amount is from about 0.1 mg/kg to about 20 mg/kg.

12. The method of claim 8, wherein the compound is administered intramuscularly.

13. The method of claim 12, wherein the effective amount is from about 1 mg/kg to about 50 mg/kg.

14. The method of claim 8, wherein the compound is administered orally.

15. The method of claim 14, wherein the effective amount is from about 5 mg/kg to about 100 mg/kg.

16. The method of claim 8, wherein the compound is administered topically.

17. The method of claim 16, wherein the effective amount is from about 0.01% w/w to about 50% w/w.

18. The method of claim 8, wherein the animal is a human.

* * * * *